United States Patent
Sakaguchi et al.

(10) Patent No.: US 11,039,815 B2
(45) Date of Patent: Jun. 22, 2021

(54) SIGNAL PROCESSING APPARATUS, CONTROL METHOD, SIGNAL PROCESSING SYSTEM, AND SIGNAL PROCESSING METHOD FOR REDUCTION OF POWER CONSUMPTION OF A WIRELESS MEDICAL DEVICE

(71) Applicant: SONY CORPORATION, Tokyo (JP)

(72) Inventors: Tatsumi Sakaguchi, Kanagawa (JP); Noboru Shibuya, Tokyo (JP)

(73) Assignee: SONY CORPORATION, Tokyo (JP)

( * ) Notice: Subject to any disclaimer, the term of this patent is extended or adjusted under 35 U.S.C. 154(b) by 1209 days.

(21) Appl. No.: 15/150,993

(22) Filed: May 10, 2016

(65) Prior Publication Data
US 2016/0249886 A1  Sep. 1, 2016

Related U.S. Application Data

(63) Continuation of application No. 13/545,777, filed on Jul. 10, 2012, now abandoned.

(30) Foreign Application Priority Data

Jul. 21, 2011  (JP) ............................. JP2011-159718

(51) Int. Cl.
*A61B 8/08* (2006.01)
*A61B 8/00* (2006.01)

(52) U.S. Cl.
CPC .......... *A61B 8/5207* (2013.01); *A61B 8/4254* (2013.01); *A61B 8/54* (2013.01); *A61B 8/56* (2013.01)

(58) Field of Classification Search
CPC ....... A61B 8/4254; A61B 8/5207; A61B 8/54; A61B 8/56
See application file for complete search history.

(56) References Cited

U.S. PATENT DOCUMENTS

| 6,083,168 | A | 7/2000 | Hossack et al. | |
|---|---|---|---|---|
| 6,471,651 | B1 * | 10/2002 | Hwang | A61B 8/00 600/437 |
| 2005/0228284 | A1 * | 10/2005 | Baumgartner | A61B 5/6844 600/459 |
| 2007/0078345 | A1 | 4/2007 | Mo et al. | |
| 2010/0286527 | A1 | 11/2010 | Cannon et al. | |
| 2011/0203374 | A1 * | 8/2011 | Oshiki | A61B 8/56 73/602 |
| 2012/0179035 | A1 * | 7/2012 | Boudier | A61B 8/4254 600/439 |
| 2012/0232397 | A1 * | 9/2012 | Ohshima | A61B 8/546 600/447 |
| 2014/0236001 | A1 * | 8/2014 | Kondou | A61B 8/4254 600/424 |

FOREIGN PATENT DOCUMENTS

| JP | 07-124156 A | 5/1995 |
|---|---|---|
| JP | 2002-095640 A | 4/2002 |
| JP | 2008-253500 A | 10/2008 |

* cited by examiner

*Primary Examiner* — Amelie R Davis
(74) *Attorney, Agent, or Firm* — Chip Law Group

(57) ABSTRACT

There is provided a signal processing apparatus including a signal processor for processing a signal to be received from or to be transmitted to a vibrator constituting a probe, and a controller for controlling a signal processing parameter of the signal processor to lower a performance of the signal processor when a motion parameter showing a characteristic of a motion of the probe is large.

14 Claims, 14 Drawing Sheets

FIG. 4
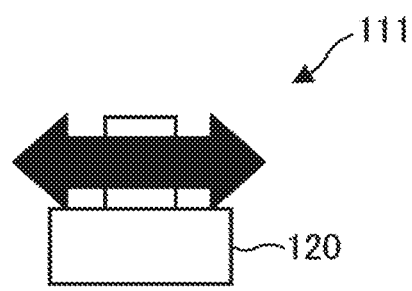
A
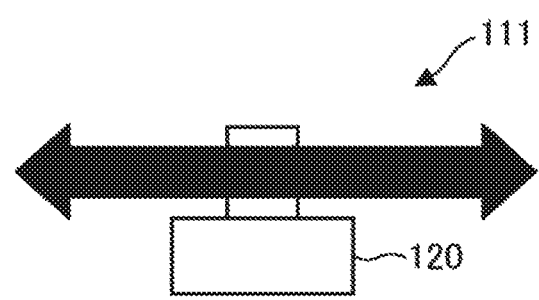
B

FIG. 5

| VIBRATOR | PROBE | WIRELESS TRANSMISSION | | | | ULTRASONIC WAVE TRANSMISSION/RECEPTION | | INTERNAL SIGNAL PROCESSING | | RESULT |
|---|---|---|---|---|---|---|---|---|---|---|
| PRESSURE | SPEED | FRAME RATE | RESOLUTION | BIT RATE | ERROR CORRECTION | NUMBER OF TRANS-MISSION BEAMS | NUMBER OF TRANSMISSION /RECEPTION VIBRATORS | AD BIT LENGTH | AD SAMPLING RATE | |
| 0 | NOT APPLIED | — | × | × | × | × | × | × | × | × | EQUIVALENT TO OFF |
| 1 | APPLIED | SPEED 1 (FASTEST) | △ | △ | △ | △ | △ | △ | △ | △ | MINIMUM (GEL OR THE LIKE APPLIED) |
| 2 | APPLIED | SPEED 2 | ○ | △ | △ | △ | △ | △ | △ | △ | |
| 3 | APPLIED | SPEED 3 | ○ | ○ | ○ | △ | △ | △ | △ | △ | |
| 4 | APPLIED | SPEED 4 | ○ | ○ | ○ | △ | △ | △ | △ | △ | |
| 5 | APPLIED | SPEED 5 | ○ | ○ | ○ | ○ | △ | △ | △ | △ | |
| 6 | APPLIED | SPEED 6 | ○ | ○ | ○ | ○ | △ | △ | △ | △ | |
| 7 | APPLIED | SPEED 7 | ○ | ○ | ○ | ○ | ○ | ○ | △ | △ | |
| 8 | APPLIED | SPEED 8 | ○ | ○ | ○ | ○ | ○ | ○ | ○ | △ | |
| 9 | APPLIED | SPEED 9 (SLOWEST) | ○ | ○ | ○ | ○ | ○ | ○ | ○ | ○ | |

GREATER IMPACT ON IMAGE QUALITY ↕ SMALLER IMPACT ON IMAGE QUALITY

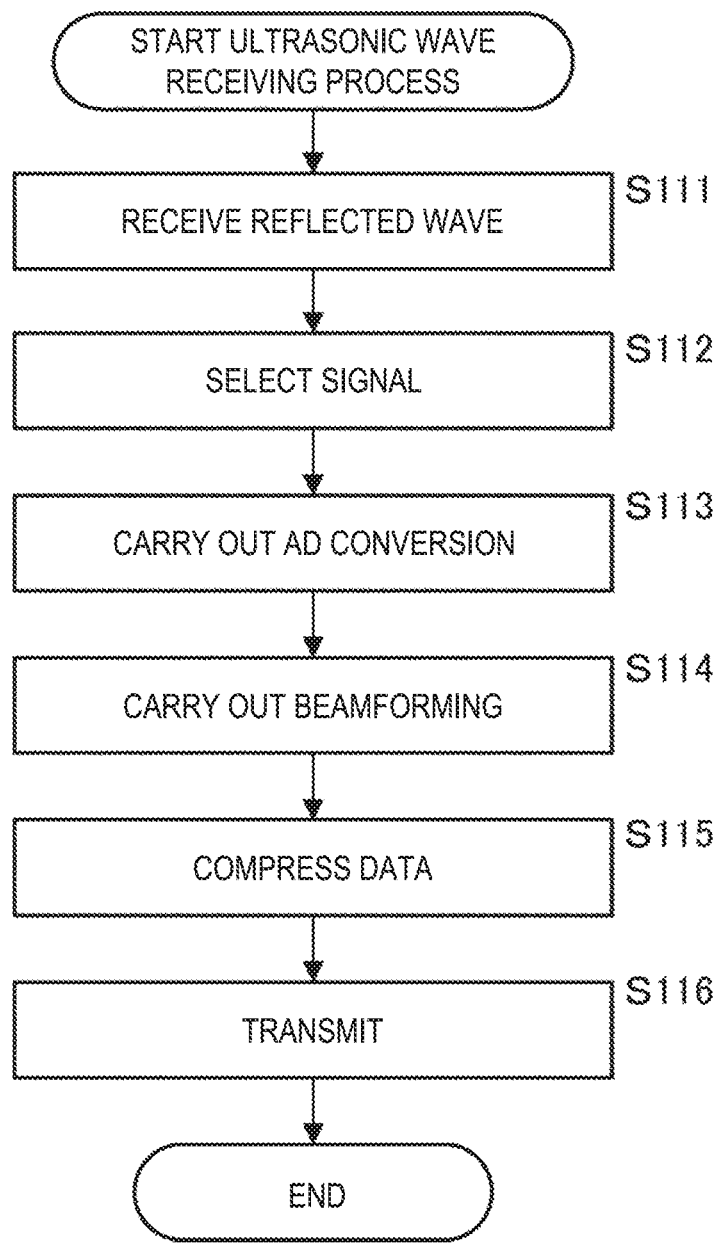

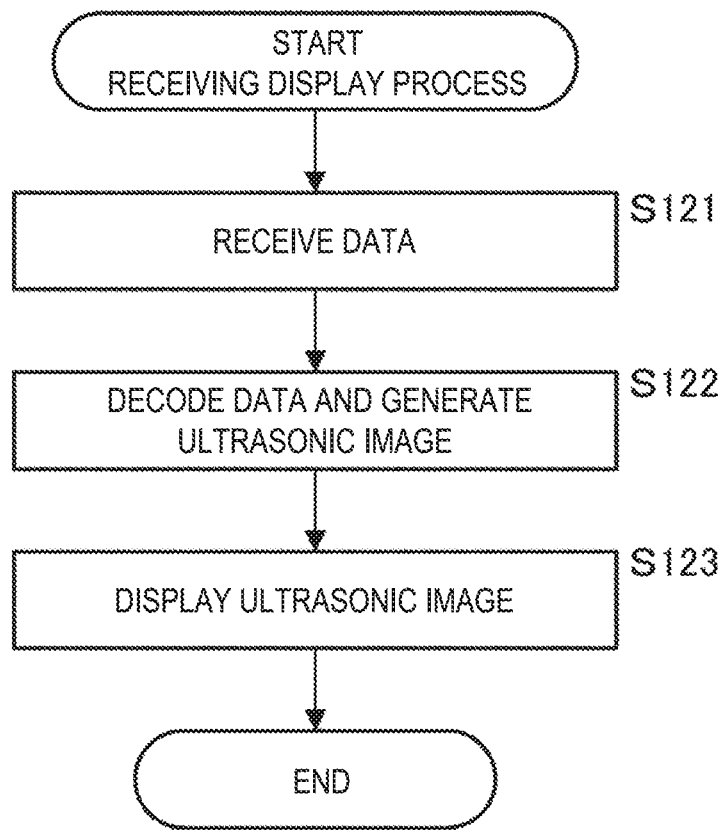

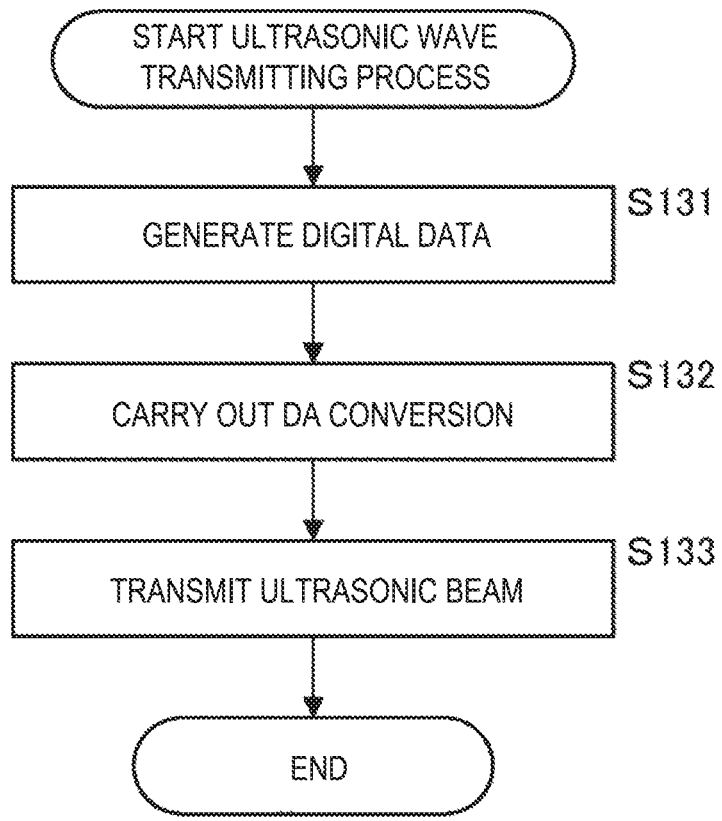

SIGNAL PROCESSING APPARATUS, CONTROL METHOD, SIGNAL PROCESSING SYSTEM, AND SIGNAL PROCESSING METHOD FOR REDUCTION OF POWER CONSUMPTION OF A WIRELESS MEDICAL DEVICE

CROSS-REFERENCE TO RELATED APPLICATIONS

The present application is a continuous application of U.S. patent application Ser. No. 13/545,777 filed Jul. 10, 2012, which is related to and claims priority benefit of Japanese Priority Patent Application JP 2011-159718 filed in the Japan Patent Office on Jul. 21, 2011, the entire content of which is hereby incorporated by reference.

BACKGROUND

The present disclosure relates to signal processing apparatuses, control methods, signal processing systems, and signal processing methods, especially, relates to a signal processing apparatus, a control method, a signal processing system, and a signal processing method which are capable of reducing electric power for use in signal processing.

In the related art, with regard to ultrasonic diagnostic apparatuses which carry out shooting of ultrasonic images, there have been some proposals in which a sensor or a switch is provided to a probe to stop/resume transmission/reception in order to reduce the necessary electric power for transmission/reception during the use of the wireless probe (see JP 2008-253500 A).

The proposed switching methods are, for example, a technique providing a physical switch, a technique detecting a position of the probe, or a technique detecting a motion of the prove. With these techniques, a timing at which the probe is not used for diagnosis is detected, and failure of turning off of the probe is prevented.

SUMMARY

However, the above proposals make no reference to an amount of the electric power during the use of the probe. Therefore, even if the proposed methods are used, the probe typically operates under the same condition when a technician or a doctor as a user holds the probe (in some cases, during the probe is placed in contact with a patient).

The present disclosure has been realized in view of the above circumstances, and is capable of reducing the electric power for use in signal processing when ultrasonic images are generated.

According to one aspect of the present disclosure, there is provided a signal processing apparatus including: a signal processor for processing a signal to be received from or to be transmitted to a vibrator constituting a probe; and a controller for controlling a signal processing parameter of the signal processor to lower a performance of the signal processor when a motion parameter showing a characteristic of a motion of the probe is large.

According to another aspect of the present disclosure, there is provided a control method performed by a signal processing apparatus, which includes a signal processor for processing a signal to be received from or to be transmitted to a vibrator constituting a probe, the control method including controlling a signal processing parameter of the signal processor to lower a performance of the signal processor when a motion parameter showing a characteristic of a motion of the probe is large.

According to another aspect of the present disclosure, there is provided a signal processing system including: a first signal processing apparatus including: a signal processor for processing a signal to be received from or to be transmitted to a vibrator constituting a probe; a controller for controlling a signal processing parameter of the signal processor to lower a performance of the signal processor when a motion parameter showing a characteristic of a motion of the probe is large; and a transmitter for transmitting the signal processed by the signal processor; and a second signal processing apparatus including: a receiver for receiving the signal from the first signal processing apparatus; and a generator for generating an ultrasonic image based on the signal received by the receiver.

According to another aspect of the present disclosure, there is provided a signal processing method performed by a first signal processing apparatus, which includes a signal processor for processing a signal to be received from or to be transmitted to a vibrator constituting a probe, the signal processing method including controlling a signal processing parameter of the signal processor to lower a performance of the signal processor when a motion parameter showing a characteristic of a motion of the probe is large, processing the signal to be received from or to be transmitted to the vibrator, and transmitting the processed signal, and the signal processing method performed by a second signal processing apparatus, including receiving the signal from the first signal processing apparatus, and generating an ultrasonic image based on the received signal.

According to one aspect of the present disclosure, a signal processing parameter of a signal processor is controlled to lower a performance of the signal processor which processes a signal to be transmitted to or to be received from a vibrator constituting a probe when a motion parameter showing a characteristic of a motion of the probe is large.

According to another aspect of the present disclosure, a signal processing parameter of a signal processor is controlled to lower a performance of the signal processor which processes a signal to be received from or to be transmitted to a vibrator constituting a prove when a motion parameter showing a characteristic of a motion of the probe is large. Further, the transmitted signal is received and an ultrasonic image is generated based on the received signal.

According to the present disclosure, when an ultrasonic image is generated, the electric power for use in signal processing can be reduced.

BRIEF DESCRIPTION OF THE DRAWINGS

FIG. 4 is a diagram illustrating a motion of the probe unit;

FIG. 5 is a diagram illustrating a relationship between an output of a sensor and a signal processing parameter;

FIG. 6 is a flowchart illustrating an example of an ultrasonic wave receiving process of a probe unit;

FIG. 7 is a flowchart illustrating an example of a reception displaying process of a reception display unit;

FIG. 8 is a flowchart illustrating an example of an ultrasonic wave transmitting process of the probe unit;

DETAILED DESCRIPTION OF THE EMBODIMENT(S)

Hereinafter, preferred embodiments of the present disclosure (hereinafter, referred to as embodiments) will be described. Note that the description will be carried out in the following order.
1. First Embodiment (a probe having a built-in acceleration sensor)
2. Second Embodiment (a probe having a built-in angle sensor)

First Embodiment

[Exemplary Configuration of Signal Transmitting System]

Figure 1:
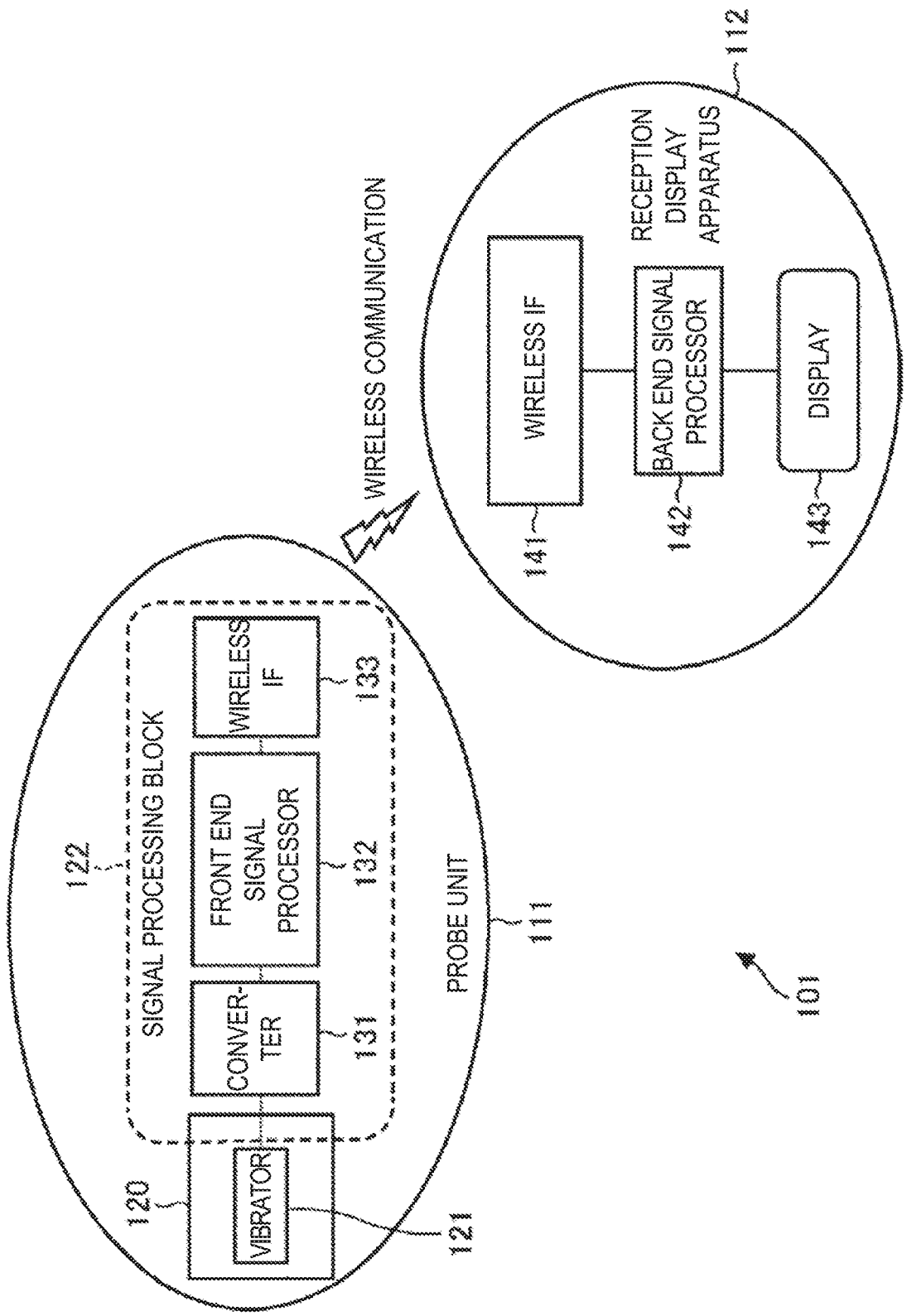
FIG. 1 is a block diagram showing an exemplary configuration of a signal processing system to which the present technology is applied.

FIG. 1 is a block diagram showing an exemplary configuration of a signal processing system to which the present technology is applied.

A signal processing system 101 shown in FIG. 1 shoots an image of the inside of an object (that is, an ultrasonic image) by using an ultrasonic wave and displays the image. The signal processing system 101 is used for medical purpose such as shooting of the inside of a patient's body or an unborn baby, or used for industrial purpose such as shooting of a cross-section of the inside of a product.

The signal processing system 101 includes a probe unit 111 and a reception display apparatus 112. The probe unit 111 and the reception display apparatus 112 carry out transmission/reception of data in wireless communication, for example. Note that the wireless communication system is not particularly limited if a sufficient band for transmission/reception of data is ensured. Also, the communication system may not only be the wireless system, but also be a wired system.

The probe unit 111 includes a probe 120 and a signal processing block 122. The probe 120 is a portion which is pressed to the skin of the object or the like and includes a plurality of vibrators 121 called as ultrasonic transducer in its inside. The probe 120 includes the vibrators 121 of 64 channels or 128 channels, for example. Note that the number of vibrators 121 included in the probe 120 is not limited.

The vibrator 121 transmits an ultrasonic beam (hereinafter, may be referred to as a transmission wave) toward the object based on a signal from the signal processing block 122. The vibrator 121 receives a reflected wave (hereinafter, may be referred to as a received wave) from the object, and provides the received signal to the signal processing block 122.

The signal processing block 122 is a block which processes the signals to or from the vibrator 121. The signal processing block 122 includes a converter 131, a front end signal processor 132, and a wireless IF (interface) 133.

The converter 131 includes an AD (Analog/Digital) converter 162 in FIG. 2, and a DA (Digital/Analog) converter 182 in FIG. 3, which will be described later. The converter 131 converts the reflected wave from the vibrator 121 into digital data, and provides the converted digital data to the front end signal processor 132. The converter 131 converts digital data from the front end signal processor 132 into an analog signal, and provides the converted analog signal to the vibrator 121.

The front end signal processor 132 carries out signal processing such as a beamforming process, a signal compressing process, and an error correcting process with respect to the digital data from the converter 131, and provides the processed data to the wireless IF 133. The front end signal processor 132 generates digital data which will be a base of a transmission wave that the vibrator 121 transmits, and provides the generated data to the converter 131.

The wireless IF 133 transmits data from the front end signal processor 132 to the reception display apparatus 112 in wireless communication.

The reception display apparatus 112 includes a wireless IF 141, a back end signal processor 142, and a display 143.

The wireless IF 141 receives data from the probe unit 111, and provides the data to the back end signal processor 142.

The back end signal processor 142 decodes compressed data transmitted from the wireless IF 141. The back end signal processor 142 generates an ultrasonic image which reflects the inside of the object based on the decoded data. The back end signal processor 142 provides the generated ultrasonic image to the display 143.

The display 143 displays the ultrasonic image generated by the back end signal processor 142.

Note that the configuration of the probe unit 111 in the example of FIG. 1 is simplified and shown, and processors or mechanical parts which are less relevant to the present technology are omitted.

[Exemplary Configuration of Probe Unit in Receiving Process]

Figure 2:
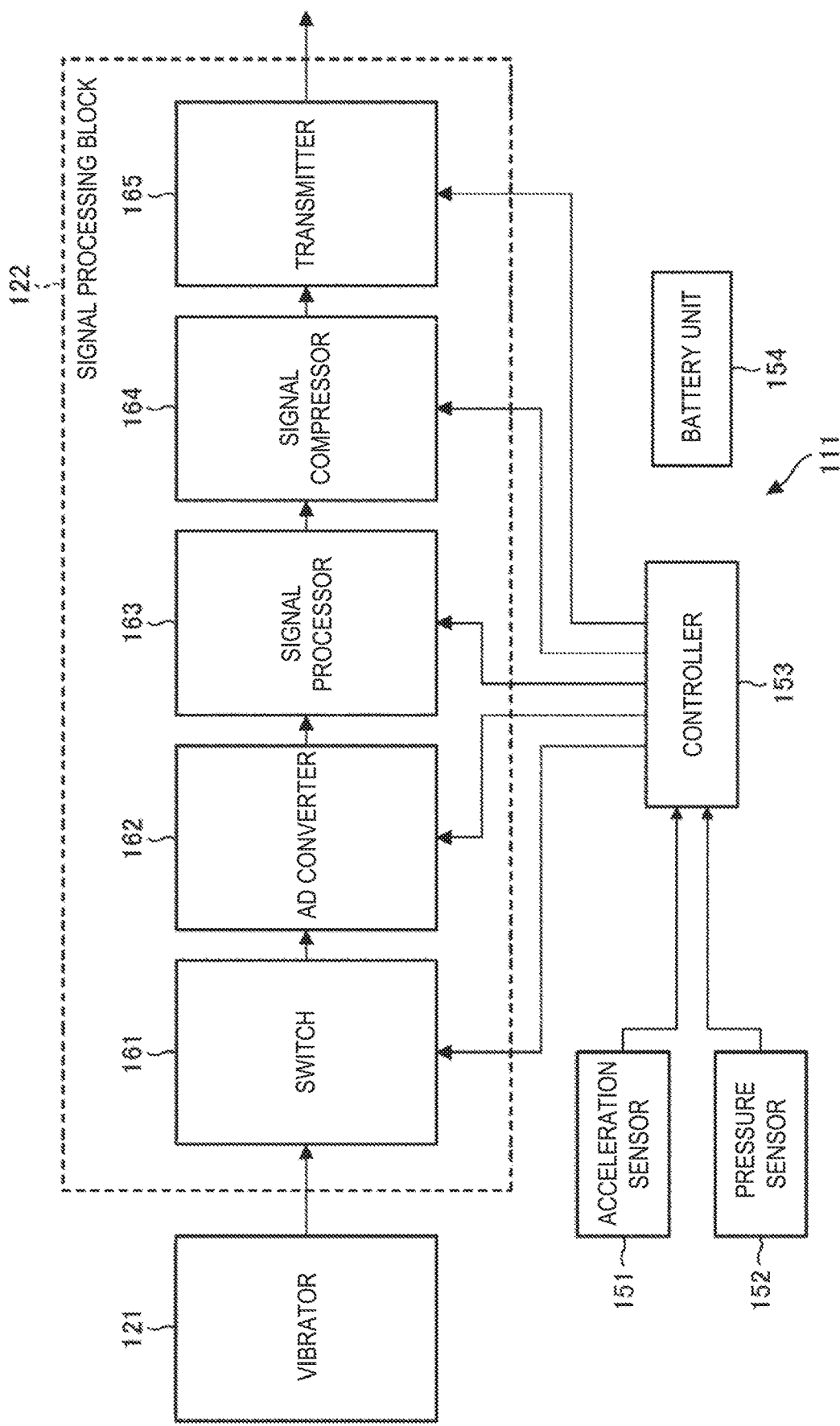
FIG. 2 is a block diagram showing an exemplary configuration of a probe unit when a receiving process is carried out.

FIG. 2 is a block diagram showing an exemplary configuration of a probe unit when a receiving process of an ultrasonic wave is carried out.

The probe unit 111 in the example shown in FIG. 2 includes a vibrator 121, a signal processing block 122, an acceleration sensor 151, a pressure sensor 152, a controller 153, and a battery unit 154.

The signal processing block 122 when carrying out a receiving process of an ultrasonic wave includes a switch 161, an AD converter 162, a signal processor 163, a signal compressor 164, and a transmitter 165. The signal processor 163, the signal compressor 164, and the transmitter 165 in the signal processing block 122 in FIG. 2 correspond to the front end signal processor 132 in FIG. 1.

The vibrator 121 receives a reflected wave from the object, and provides the received signal to the switch 161 in the signal processing block 122.

The switch 161 determines which signal is to be read from among the signals received by each vibrator of the vibrator 121 and selects the signal under control of the controller 153. When the vibrator 121 includes 128 channels and reads 32 channel signals, for example, the switch 161 determines which 32 channel signals are to be read from among the 128 channels and selects them. The switch 161 reads the selected signals, and provides the read signals to the AD converter 162.

The AD converter 162 carries out an AD convert of the signal from the switch 161 under control of the controller 153. The AD converter 162 provides the converted digital data to the signal processor 163.

The signal processor 163 carries out a beamforming process of the digital data from the AD converter 162 under control of the controller 153. The signal processor 163 also carries out signal processing such as image enhancement or noise reduction or the like of the data after the beamforming process (hereinafter, referred to as RF data) as necessary. The signal processor 163 provides the processed data to the signal compressor 164.

The signal compressor 164 compresses the digital data from the signal processor 163 into a prescribed compressed format under control of the controller 153. The signal compressor 164 provides the compressed data to the transmitter 165. Note that the compressed format is not limited.

The transmitter 165 makes an addition to the data from the signal compressor 164 such as a redundant error correcting code for transmission error compensation under control of the controller 153, and transmits the data to the reception display apparatus 112 via the wireless IF 133 shown in FIG. 1. The transmitter 165 retransmits the data in order to compensate a transmission error.

The acceleration sensor 151 is provided in the probe 120 or in the probe unit 111. The acceleration sensor 151 detects a motion of the probe 120 by the user, and provides a motion parameter which is information showing a characteristic of the motion of the probe 120 to the controller 153. For example, the acceleration sensor 151 provides the motion parameter which shows a characteristic of the motion as a speed of the probe 120 to the controller 153. Note that the motion parameter is not limited to the speed if the parameter shows any motion characteristic such as a travel amount or a magnitude of the motion of the probe 120.

The pressure sensor 152 is provided at a contact surface against skin of the object within the probe 120. The pressure sensor 152 detects a pressure that the skin of the object or the like is pressed to the probe 120, and provides information of the detected pressure to the controller 153.

The battery unit 154 is configured with a rechargeable battery and the like, and supplies the electric power to each part of the probe unit 111.

The controller 153 controls operations of the each part which constitutes the signal processing block 122 in response to the information detected by the acceleration sensor 151 and the pressure sensor 152 in order to reduce the electric power consumption accumulated in the battery unit 154. That is, the controller 153 changes a processing parameter of the each part which constitutes the signal processing block 122 in response to the information detected by the acceleration sensor 151 and the pressure sensor 152 to lower a performance of the each part which constitutes the signal processing block 122.

Here, the performance referred in the present disclosure means processing a speed, an operation clock (a frequency), a data transmission speed, the number of cores in use for a processor assigned to each process, the number of threads in software processing or the like.

That is, lowering a performance means reducing the electric power consumption in such a way as to delay the processing the speed, to reduce the operation clock, to delay the transmission speed, to decrease the number of cores in use for a processor, and to decrease the number of threads.

Lowering a performance means, more specifically, controlling the processing parameter of the each part which constitutes the signal processing block 122 to reduce the electric power consumption.

In the signal processing block 122, the processing parameter in signal processing is, described further in details later, for example, an external signal processing parameter, an ultrasonic signal processing parameter, an internal signal processing parameter. The external signal processing parameter is a parameter that is used in signal processing in relation to transmission. The ultrasonic signal parameter is a parameter that is used in signal processing in relation to ultrasonic processing, and the internal signal processing parameter is a parameter that is used in signal processing in relation to AD or DA conversion.

Back to FIG. 2, the controller 153 controls the switch 161, for example, to change the number of vibrators 121 which are used for receiving. To increase SN of a received signal, it is common to use information from a plurality of vibrators 121. By decreasing the number of channels of the vibrators 121 that are used for receiving, an amount of data processing in the signal processor 163 described later can be reduced. As a result, the electric power consumption can be reduced.

The controller 153 controls the AD converter 162, for example, to change a bit length of digital data or a sampling frequency when an analog signal of each received channel is converted into digital data.

Note that the signal processing system 101 is often used for CAD (Computer Aided Diagnosis) of medical images. If a high sampling frequency is sampled, an amount of acquired signal information increases, and higher precision beamforming can be carried out. As a result, image quality is enhanced. Therefore, sampling a high sampling frequency leads to enhancement of diagnosis ability of CAD.

However, a high frequency in AD conversion causes an increase of data and affects later signal processing amount. When the system is not used for CAD, that is, the system is used for normal diagnosis or the like, such high quality image is not necessary. Therefore, in the normal diagnosis, lowering the sampling frequency reduces the electric power consumption of the AD converter 162 itself as well as reducing the data processing amount of signal processing. As a result, the electric power consumption can be reduced. In the AD converter 162, shortening the bit length of digital data may also achieve a similar effect to lowering the sampling frequency.

The controller 153 controls the signal processor 163 to change parameters in relation to electric power from among the parameters in beamforming processing, such as the number of reception focal points, and a sampling frequency of RF data.

By decreasing the number of reception focal points or the sampling frequency of RF data, reduction of the process itself or of the amount of data passed on to the next process can be achieved, and as a result, the electric power consumption can be reduced.

Note that an ON/OFF in signal processing such as image enhancement or noise reduction in the signal processor 163, or control of complexity of an algorithm or the like may also affect the electric power. The controller 153 may control such processes.

The controller 153 controls the signal compressor 164, for example, to change a data compression ratio. By increasing the data compression ratio, a data amount to be transmitted from the probe unit 111 to the reception display apparatus 112 can be reduced, and as a result, the electric power in transmission can be reduced.

The controller 153 controls the transmitter 165, for example, to change a degree of an addition of an error correcting code or whether or not the error correction is added. By lowering the degree of the error correction or not using the error correction function itself, the electric power consumption in transmission can be reduced. Further, having the transmitter 165 change acceptance of retransmission demand, which is caused by the operation in cooperation with the reception display apparatus 112, into refusal also leads to reduction of the electric power consumption.

[Exemplary Configuration of Probe Unit in Transmitting Process]

Figure 3:
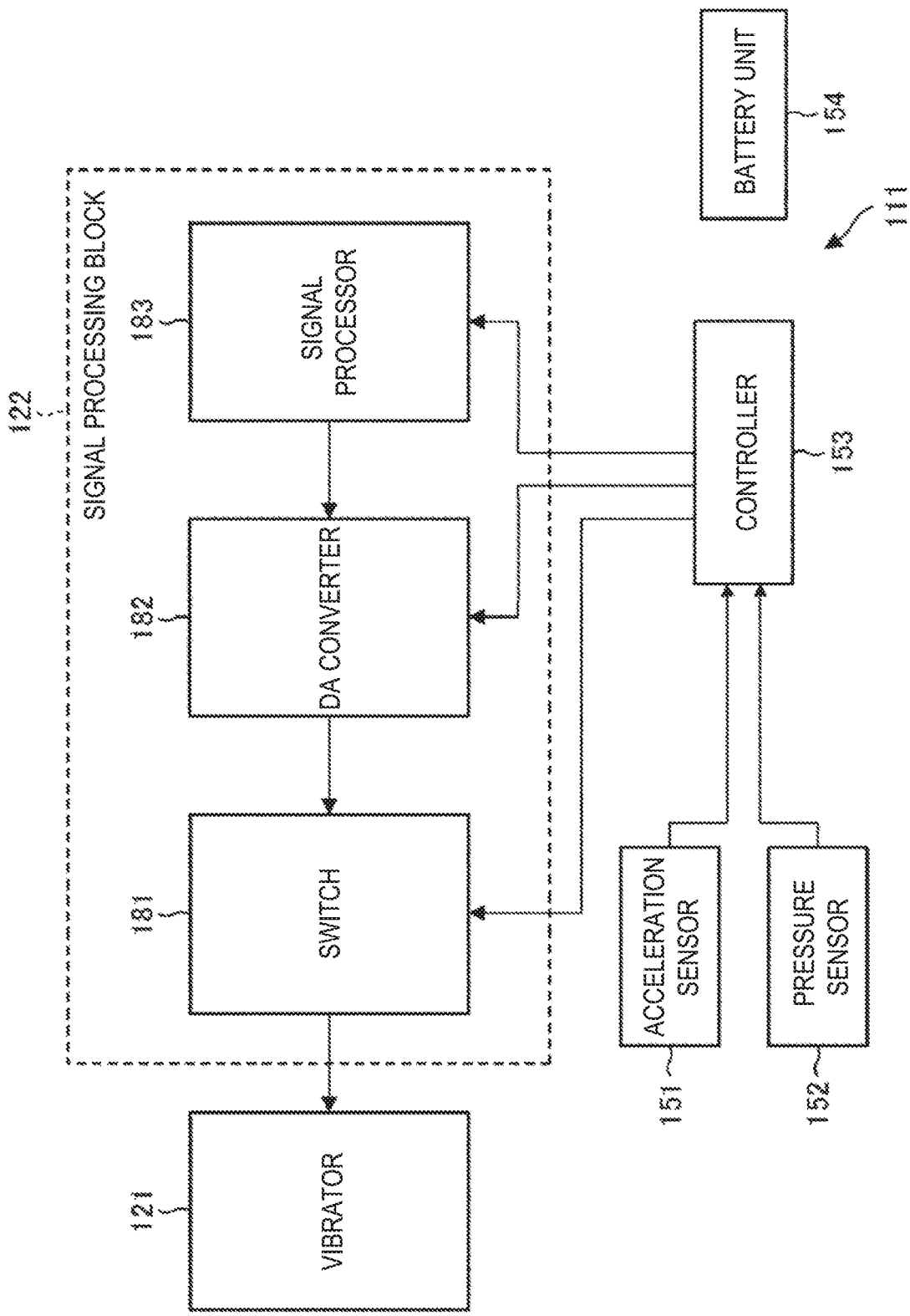
FIG. 3 is a block diagram showing an exemplary configuration of the probe unit when a transmitting process is carried out.

FIG. 3 is a block diagram showing an exemplary configuration of the probe unit when a transmitting process is carried out.

In the example of FIG. 3, a probe unit 111 includes a vibrator 121, a signal processing block 122, an acceleration sensor 151, a pressure sensor 152, a controller 153, and a battery unit 154 like the probe unit 111 of FIG. 2. Note that corresponding elements are denoted with corresponding reference signs, and repeated explanation is omitted.

The signal processing block 122 when carrying out a transmitting process of an ultrasonic wave includes a switch 181, a DA converter 182, and a signal processor 183 unlike the signal processing block 122 of FIG. 2. The signal processor 183 in the signal processing block 122 of FIG. 3 corresponds to the front end signal processor 132 of FIG. 1.

The switch 181 selects the vibrator 121 based on an analog signal from the DA converter 182. That is, the switch 181 selects a combination of the vibrators to be operated from among a plurality of vibrators which constitute the vibrator 121. The switch 181 vibrates the selected vibrator 121 by connecting the selected vibrator 121 and transmitting a signal. Consequently, an ultrasonic beam is transmitted from the vibrator 121 to the object.

The DA converter 182 converts digital data from the signal processor 183 into an analog signal, and provides it to the switch 181.

The signal processor 183 generates digital data which will be a base of an ultrasonic beam that the vibrator 121 transmits to the object. The signal processor 183 provides the generated digital data to the DA converter 182.

The controller 153 in the example of FIG. 3 also controls operation of each part which constitutes the signal processing block 122 in response to information detected by the acceleration sensor 151 and the pressure sensor 152 in order to reduce battery consumption of the battery unit 154. That is, the controller 153 changes a processing parameter of the each part which constitutes the signal processing block 122 in response to the information detected by the acceleration sensor 151 and the pressure sensor 152 to lower a performance of the each part which constitutes the signal processing block 122.

However, unlike the case of the receiving process in FIG. 2, the switch 181, the DA converter 182, and the signal processor 183 basically operate in cooperation with each other in the transmitting process in FIG. 3.

The digital data generated in the signal processor 183 uniquely determines a bit length of digital data transmitted through the DA converter 182, a sampling frequency, and the number of lines (the number of vibrators to be operated), and also determines a combination of the vibrators 121 connected (vibrated) by the switch 181.

That is to say, the signal processor 183 uniquely determines the bit length of the digital data transmitting through the DA converter 182, the sampling frequency, and the number of lines, and the combination of the vibrator 121 connected by the switch 181, and generates digital data based on the determined parameter combination.

Therefore, in the case of the transmitting process, the controller 153 controls the signal processor 183 to change the bit length of the digital data transmitted through the DA converter 182, the sampling frequency, and the number of lines, the combination of the vibrator 121 connected by the switch 181 and the like.

In the signal processor 183, by shortening the bit length of the digital data, lowering the sampling frequency, the DA conversion process can be reduced. Further, by decreasing the number of lines, the electric power for ultrasonic wave transmission can be reduced.

As described above, the controller 153 controls each signal processor which constitutes the signal processing block 122 to lower its performance in order to reduce the battery consumption of the battery unit 154 either in the receiving process or in the transmitting process of an ultrasonic wave.

At this point, the controller 153 controls an ON/OFF of the each part which constitutes the signal processing block 122 in response to the information of the pressure detected by the pressure sensor 152. The controller 153 changes the performance of the parameter of the each part which constitutes the signal processing block 122 in response to a magnitude of the motion parameter as the motion information detected by the acceleration sensor 151.

Example of Probe Motion

FIG. 4 is a diagram illustrating a motion of the probe.

The user holds the probe unit 111 which includes the probe 120, moves the probe 120 with pressing it to the object, and checks an ultrasonic image displayed on the reception display unit 112. At that time, motion patterns of the probe 120 by the user are classified roughly into the following two cases.

When a position of the probe 120 approaches a point on the object that the user wishes to check in details as shown in FIG. 4A, the user tends to move the probe unit 111 slowly within a small area. That is, when the motion of the probe 120 is small, the speed is slow, or the travel amount is small, there is a high possibility that the position of the probe 120 have approached the point that the user wishes to check in details. Therefore, in this case, it is desirable that the image quality is as high as possible.

On the other hand, when a point that the user wishes to check in details is searched for within a broad area, as shown in FIG. 4B, the user tends to move the probe unit 111 quickly within a broad area. That is, when the motion of the probe 120 is large, the speed is quick, or the travel amount is large, there is a high possibility that the user still searches the broad area for the point that the user wishes to check in details. Therefore, in this case, the image quality can be lower than that of the case of FIG. 4A.

According to the above, the controller 153 changes the processing parameter of the each part to lower the performance of the processing parameter of the each part which constitutes the signal processing block 122 when the motion parameter (the speed, the travel amount, or the magnitude of the motion) as the motion information of the probe 120 is large.

On the other hand, the controller 153 changes the processing parameter of the each part to return (or increase) the performance back to normal of the processing parameter of the each part which constitutes the signal processing block 122 when the motion parameter (the speed, the travel amount, or the magnitude of the motion) as the motion information of the probe 120 is small.

Consequently, even in the middle of diagnosis using the signal processing system 101, the electric power consumption can be reduced. As a result, the life of the electric power accumulated in the battery unit 154 provided in the probe unit 111 can be increased.

Note that, as the user holds and moves the probe unit 111, the probe 120 also moves. Therefore, hereinafter, the description will be carried as the motion of the probe 120 and the motion of the probe unit 111 are deemed to have the same meaning.

Example of Combination of Parameters

FIG. 5 is a diagram illustrating a relationship between an output of a sensor and a control of a parameter of each part.

The first column from the left in the example of FIG. 5 represents numbers of combination patterns of the processing parameters. The second and third columns from the left represent degrees of the outputs from the sensors. The fourth to eleventh columns from the left represent control statuses of the processing parameters of the each part of the signal processing block 122. The first column from the right shows results of the outputs of the sensors and the control.

To be more specific, the second column from the left represents whether or not there is a pressure on the vibrator, which is detected by the pressure sensor 152. The third column from the left represents the level of the speed as the motion parameter of the probe 120, which is detected by the acceleration sensor 151.

As for the fourth to eleventh columns from the left, the columns represent, starting from the left, the control statuses of four wireless transmission parameters, two ultrasonic wave transmission/reception parameters, and two internal signal processing parameters.

The order of these parameters shows a degree of an impact to the image quality. The further in the left the parameter aligns, the greater impact on the image quality. On the other hand, the further in the right the parameter aligns, the smaller impact on the image quality. That is, among the wireless transmission parameter, the ultrasonic wave transmission/reception parameter, and the internal signal processing parameter, the wireless transmission parameter has the greatest impact on the image quality, whilst the internal signal processing parameter has the smallest impact on the image quality.

The wireless transmission parameter is the signal processing parameter that is used in signal processing in relation to transmission with outside. In the example of FIG. 5, the frame rate, the resolution, the bit rate, and the error correction are included in the wireless transmission parameter. Note that, among the four processing parameters, the frame rate has the greatest impact on the image quality, whilst the error correction has the smallest impact on the image quality.

The wireless transmission parameter is used only in the receiving process. The frame rate and the resolution are the processing parameters for the signal processor 163. The bit rate is the processing parameter for the signal compressor 164, and the error correction is the processing parameter for the transmitter 165.

The ultrasonic wave transmission/reception parameter is the ultrasonic signal processing parameter that is used in signal processing in relation to ultrasonic processing. In the example of FIG. 5, the number of transmission beams and the number of transmission/reception vibrators are included in the ultrasonic wave transmission/reception parameter. The number of transmission beams has a greater impact on the image quality compared to that of the number of transmission/reception vibrators.

In a receiving process, the number of transmission beams and the number of transmission/reception vibrators are the processing parameters for the switch 161, whilst in a transmitting process, those are the processing parameters for the signal processor 183.

The internal signal processing parameter is the signal processing parameter that is used in signal processing in relation to AD or DA conversion. In the example of FIG. 5, the AD bit length and the AD sampling rate (a sampling frequency) are included in the internal signal processing parameter. The AD sampling rate has a smaller impact on the image quality compared to that of the AD bit length.

The AD bit length and the AD sampling rate, in a receiving process, are the processing parameters for the AD converter 162, whilst are the processing parameters for the signal processor 183 in a transmitting process.

Here, x marks (cross marks) shown in FIG. 5 represent that the functions to which the processing parameters correspond (the processor) are OFF. Δ marks (triangle marks) represent that the processing parameters are controlled to be weaker, smaller, fewer and the electric power is not consumed than average, that is, the performances is controlled to be lowered. ○ marks (circle marks) represent that the processing parameters are controlled to perform standard operation.

Hereinafter, control processing of the controller 153 will be described in details with reference to FIG. 5. For example, the controller 153 determines whether or not the probe 120 of the probe unit 111 is being touched to a human body (the skin) by using an input from the pressure sensor 152. If determined that the probe 120 is not touched, the controller 153 turns OFF every function of the signal processing block 122 to reduce the electric power consumption as shown by x marks of the combination pattern 0. That is, the combination pattern 0 is a pattern which is determined roughly equal to OFF of the probe unit 111.

When it is determined, from an output of the pressure sensor 152, that some sort of pressure is applied, that is, that the probe 120 of the probe unit 111 is touched to something, the controller 153 turns ON the function of the each part of the signal processing block 122. Then, the controller 153 controls each processing parameter based on the speed as the motion parameter of the probe 120 which can be obtained from the acceleration sensor 151.

The controller 153 controls the processing parameters to save power (lower the electric power) from a processing parameter having a smaller impact on the image quality as the motion parameter of the probe 120 becomes larger, that is, the speed of the probe 120 becomes faster.

For example, the controller 153 stores the speeds 1 to 9 in a memory not shown in the drawings as thresholds of the motion parameter of the probe 120 in 9 levels. Among the speeds, the speed 1 is the fastest speed, whilst the speed 9 is the slowest speed. The controller 153 compares the stored thresholds and an output from the acceleration sensor 151.

The controller 153 controls all the processing parameters to lower the performances as shown by the combination pattern 1 when it is determined that that the speed of the probe 120 is more than the speed 1 (the fastest speed). That is, the combination pattern 1 is a pattern that is determined to be fine with the minimum electric power because this is merely a case where a gel, etc., is applied to the human body by using the probe 120 or the like.

The controller 153 controls the processing parameters except the frame rate to lower the performances as shown by the combination pattern 2 when it is determined that that the speed of the probe 120 is slower than the speed 1 and faster than the speed 2 or more. That is, the controller 153 controls the resolution, the bit rate, the error correction, the number of transmission beams, the number of transmission/reception vibrations, the AD bit length, and the AD sampling rate to lower the performances.

The controller 153 controls the processing parameters except the frame rate and the resolution to lower the performance as shown by the combination 3 when it is determined that that the speed of the probe 120 is slower than the speed 2 and faster than the speed 3 or more. That is, the controller 153 controls the bit rate, the error correction, the number of transmission beams, the number of transmission/reception vibrations, the AD bit length, and the AD sampling rate to lower the performances.

The controller 153 controls the processing parameters except the frame rate, the resolution, and the bit rate to lower the performances as shown by the combination pattern 4 when it is determined that that the speed of the probe 120 is slower than the speed 3 and faster than the speed 4 and more. That is, the controller 153 controls the error correction, the number of transmission beams, the number of transmission/reception vibrations, the AD bit length, and the AD sampling rate to lower the performance.

The controller 153 controls the processing parameters in such a way that is shown by the combination pattern 5 when it is determined that that the speed of the probe 120 is slower than the speed 4 and faster than the speed 5 and more. That is, the controller 153 controls the processing parameters except the frame rate, the resolution, the bit rate, and the error correction to lower the performances. The controller 153 controls the number of transmission beams, the number of transmission/reception vibrations, the AD bit length, the AD sampling rate to lower the performances.

The controller 153 controls the number of transmission/reception vibrations, the AD bit length, the AD sampling rate to lower the performances as shown by the combination pattern 6 when it is determined that that the speed of the probe 120 is slower than the speed 5 and faster than the speed 6 and more. That is, the controller 153 controls the processing parameters except the frame rate, the resolution, the bit rate, the error correction, and the number of transmission beams to lower the performances.

The controller 153 controls the AD bit length, and the AD sampling rate to lower the performances as shown by the combination pattern 7 when it is determined that that the speed of the probe 120 is slower than the speed 6 and faster than the speed 7 and more. That is, the controller 153 controls the processing parameters except the frame rate, the resolution, the bit rate, the error correction, the number of transmission beams, and the number of transmission/reception vibrations to lower the performances.

The controller 153 controls the AD sampling rate to lower its performance as shown by the combination pattern 8 when it is determined that that the speed of the probe 120 is slower than the speed 7 and faster than the speed 8 and more. That is, the controller 153 controls the processing parameters except the frame rate, the resolution, the bit rate, the error correction, the number of transmission beams, the number of transmission/reception vibrations, and the AD bit length to lower the performance.

The controller 153 controls all the processing parameters to perform standard operation as shown by the combination pattern 9 when it is determined that that the speed of the probe 120 is slower than the speed 8 and faster than the speed 9 (the slowest speed).

As described above, the controller 153 controls the processing parameters from the processing parameters having a smaller impact on the image quality to gradually save power as the speed of the probe 120 becomes faster (that is, the motion parameter becomes larger).

Note that the example of FIG. 5 illustrates a case that the control, when a pressure is applied, is divided into 9 levels in the combination patterns 1 to 9, and also each processing parameter is controlled by 2 values (the ○ and Δ marks). In fact, the controller 153 is capable of controlling in a non-step fashion by changing the processing parameters linearly.

Also, the example of FIG. 5 illustrates a system in which each processing parameter is aligned in the order of a degree of an impact on the image quality, and the control is applied such that the image quality gradually decreases. However, each processing parameter might be controlled independently. Note that the controller 153 may control the ultrasonic signal processing parameter, the external signal processing parameter, and the internal signal processing parameter by setting a priority as shown in the example of FIG. 5.

Further, in the signal processing system 101, it may be possible to select a parameter which is not to be controlled (not to be lowered a performance) by a request from the users, or it may also possible to change the order of control. Further, the processing parameters are not limited to the parameters shown in FIG. 5. The present technology is applicable to any parameter if the parameter is used for processing a signal received from the vibrator or a signal to be transmitted to the vibrator.

The example of FIG. 5 uses the speed of the probe 120 as the determination criterion, but the motion parameter is, as described above, not limited to the speed. A rate of acceleration or a travel amount of the probe 120 per unit time or the like can be used as the criterion if the value is obtained from an output of the acceleration sensor 151. Also, the sensor is not limited to the acceleration sensor 151.

[Flow of Ultrasonic Wave Receiving Process]

Next, an ultrasonic wave receiving process of the probe unit 111 will be described with reference to the flowchart of FIG. 6.

At step S111, the vibrator 121 receives a reflected wave from the object. The vibrator 121 provides the received signal to the switch 161 of the signal processing block 122.

At step S112, the switch 161 selects a signal. That is, the switch 161 determines which signal is to be read from among the signals received by each vibrator of the vibrator 121 and select the signal. The number of reception vibrators of this time is controlled by the controller 153 in response to a magnitude of the motion parameter from the acceleration sensor 151. The switch 161 reads the selected signal and provides the signal to the AD converter 162.

At step S113, the AD converter 162 carries out AD conversion for the signal from the switch 161 at a prescribed sampling rate. The AD (digital data) bit length and the AD sampling rate of this time is controlled by the controller 153 in response to a magnitude of the motion parameter from the acceleration sensor 151. The AD converter 162 provides the converted digital data to the signal processor 163.

At step S114, the signal processor 163 carries out a beamforming process for the digital data from the AD converter 162. The signal processor 163 carries out signal processing such as image enhancement or noise reduction for RF data under control of the controller 153. The frame rate and the resolution of this time are controlled by the controller 153 in response to a magnitude of the motion parameter from the acceleration sensor 151. The image processing such as the image enhancement or the noise reduction is also controlled by the controller 153 in response to the magnitude of the motion parameter from the acceleration sensor 151. The signal processor 163 provides the processed data to the signal compressor 164.

At step S115, the signal compressor 164 compresses the digital data from the signal processor 163 in a prescribed compressed format. The bit rate of this time is controlled by the controller 153 in response to the magnitude of the motion parameter from the acceleration sensor 151. The signal compressor 164 provides the compressed data to the transmitter 165.

At step S116, the transmitter 165 makes an addition to the data from the signal compressor 164 such as a redundant error correcting code for transmission error compensation, and transmits the data to the reception display apparatus 112 via the wireless IF 133. The addition of the error correction or the like of this time are controlled by the controller 153 in response to the magnitude of the motion parameter from the acceleration sensor 151.

As described above, an ultrasonic wave received by the probe unit 111 is subject to the series of processes, and the processed data is transmitted to the reception display apparatus 112 via wireless communication.

[Flow of Reception Display Process]

Next, a reception display process of the reception display apparatus 112 will be described with reference to the flowchart of FIG. 7.

At step S121, the wireless IF 141 receives the data transmitted at step S116 of FIG. 6. The wireless IF 141 provides the received data to the back end signal processor 142.

At step S122, the back end signal processor 142 decodes the compressed data from the wireless IF 141 in a method corresponding to the compression of the signal compressor 164, and generates an ultrasonic image reflecting the inside of the object. The back end signal processor 142 provides the generated ultrasonic image to the display 143.

At step S123, the display 143 displays the ultrasonic image.

As described above, in the reception display apparatus 112, the ultrasonic image is displayed, which corresponds to the data of the ultrasonic wave received by the probe unit 111.

[Flow of Ultrasonic Wave Transmitting Process]

Next, an ultrasonic wave transmitting process of the probe unit 111 will be described with reference to the flowchart of FIG. 8.

At step S131, the signal processor 183 generates digital data which will be a base of an ultrasonic beam to be transmitted from the vibrator 121 to the object under control of the controller 153.

That is, the signal processor 183 uniquely determines the bit length of digital data transmitting through the DA converter 182, the sampling frequency, the number of lines, and the combination of the vibrators 121 connected by the switch 181, and generates digital data based on the determined parameter combination. Each processing parameter of this time is controlled by the controller 153 in response to a magnitude of the motion parameter from the acceleration sensor 151.

The signal processor 183 provides the generated data to the DA converter 182.

At step S132, the DA converter 182 carries out DA conversion. That is, the DA converter 182 converts the digital data from the signal processor 183 into an analog signal, and provides it to the switch 181.

At step S133, the vibrator 121 transmits an ultrasonic beam to the object. That is, the switch 181 selects a vibrator 121 based on the analog signal from the DA converter 182. The switch 181 vibrates the selected vibrator 121 by connecting the selected vibrator 121 and transmitting a signal. Consequently, an ultrasonic beam is transmitted from the vibrator 121 to the object.

As described above, the ultrasonic beam is transmitted in the probe unit 111.

[Flow of Control Process]

Next, a control process of the probe unit 111 will be described with reference to the flowchart of FIG. 9.

Information of a pressure from the pressure sensor 152 is input to the controller 153. The controller 153 determines whether or not the pressure is applied to the probe 120 at step S151. When it is determined that the pressure is applied at step S151, the process proceeds to step S152. That is, step S152 is a process when it is determined that the probe 120 is used for diagnosis.

The acceleration sensor 151 detects a motion of the probe 120, and provides a motion parameter as information of the detected motion to the controller 153. At step S152, the controller 153 obtains the motion parameter from the acceleration sensor 151. At step S153, the controller 153 determines a processing parameter to be controlled to lower a performance in response to a magnitude of the obtained motion parameter, as described with reference to FIG. 5, At step S154, the controller 153 controls the processing parameter determined at step S153 to lower the performance. In doing so, among the each part of the signal processing block 122, the part which carries out a process by using the processing parameter is controlled. At this time, processing parameters which have not been determined by the process at step S153 is controlled to perform standard operation.

On the other hand, at step S151, when it is determined that that the pressure is not applied, the process proceeds to step S155. That is, step S155 is a process when it is determined that the probe 120 is not used for diagnosis.

At step S155, the controller 153 turns OFF all functions (the each part) of the signal processing block 122 to reduce the electric power consumption.

Note that, since the controller 153 is ON at this time, the functions of the signal processing block 122 are turned ON when it is determined that the pressure is applied at the next control process step S151, and the subsequent processes are repeated.

As described above, the image quality of an ultrasonic image desired by the user can be known from the motion of the probe unit 111 (the probe 120) by the user. Therefore, the probe unit 111 controls the process of the each part of the signal processing block 122 in response to the motion of the probe 120. Especially, the probe unit 111 controls the processing parameter to lower the performance in the signal processing when the motion parameter which shows a characteristic of the motion of the probe 120 is large.

Therefore, when the user moves the probe unit 111 small or slowly in order to clearly look at a position to be shot an ultrasonic image, the image quality can be preferentially enhanced over reduction of the electric power consumption.

On the other hand, when the user moves the probe unit 111 big and quickly in order to look for a position within a rough area on the body, the electric power consumption can be preferentially reduced over enhancement of the image quality.

Consequently, even when the probe unit 111 is used for diagnosis, the electric power consumption of the battery unit 154 in the probe unit 111 can be reduced. As a result, the life of the battery unit 154 can be increased.

Figure 9:
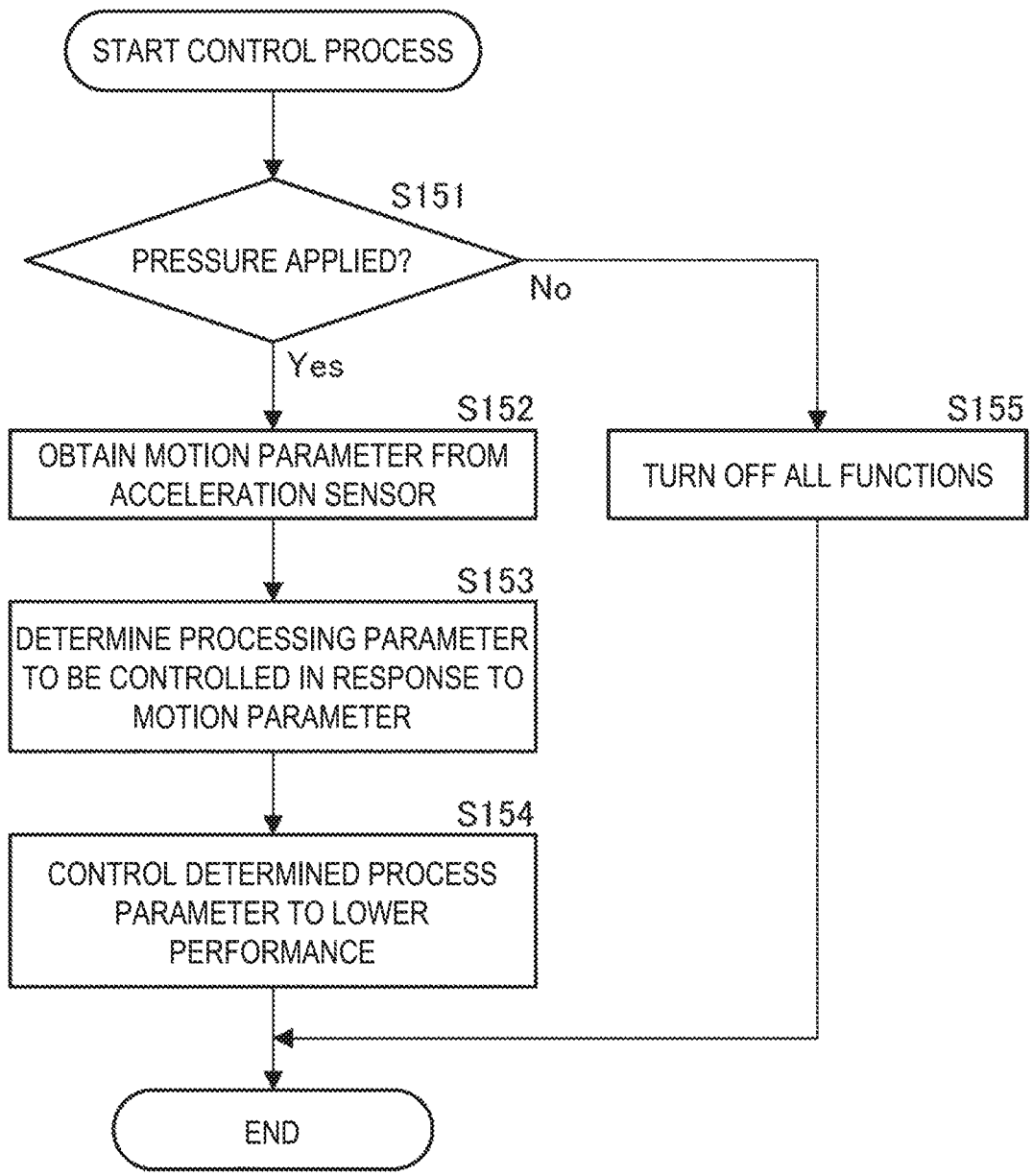
FIG. 9 is a flowchart illustrating an example of a control process in the probe unit.

Note that the example of FIG. 9 uses the output from the pressure sensor 152 as the criterion for determining whether or not the probe 120 is pressed to the human body. It may also possible to use echo intensity from a depth of the received ultrasonic wave to determine whether or not the probe 120 is pressed to the human body. This is because when a contact surface of the probe exposes the air, that is, when the contact surface is not touched to the human body via a gel or the like, all ultrasonic waves are reflected at a boundary between the contact surface and the air. This nature that the echo from the depth (a point distant from the probe) is not observed is exploitable.

Second Embodiment

[Exemplary Configuration of Probe Unit]

Figure 10:
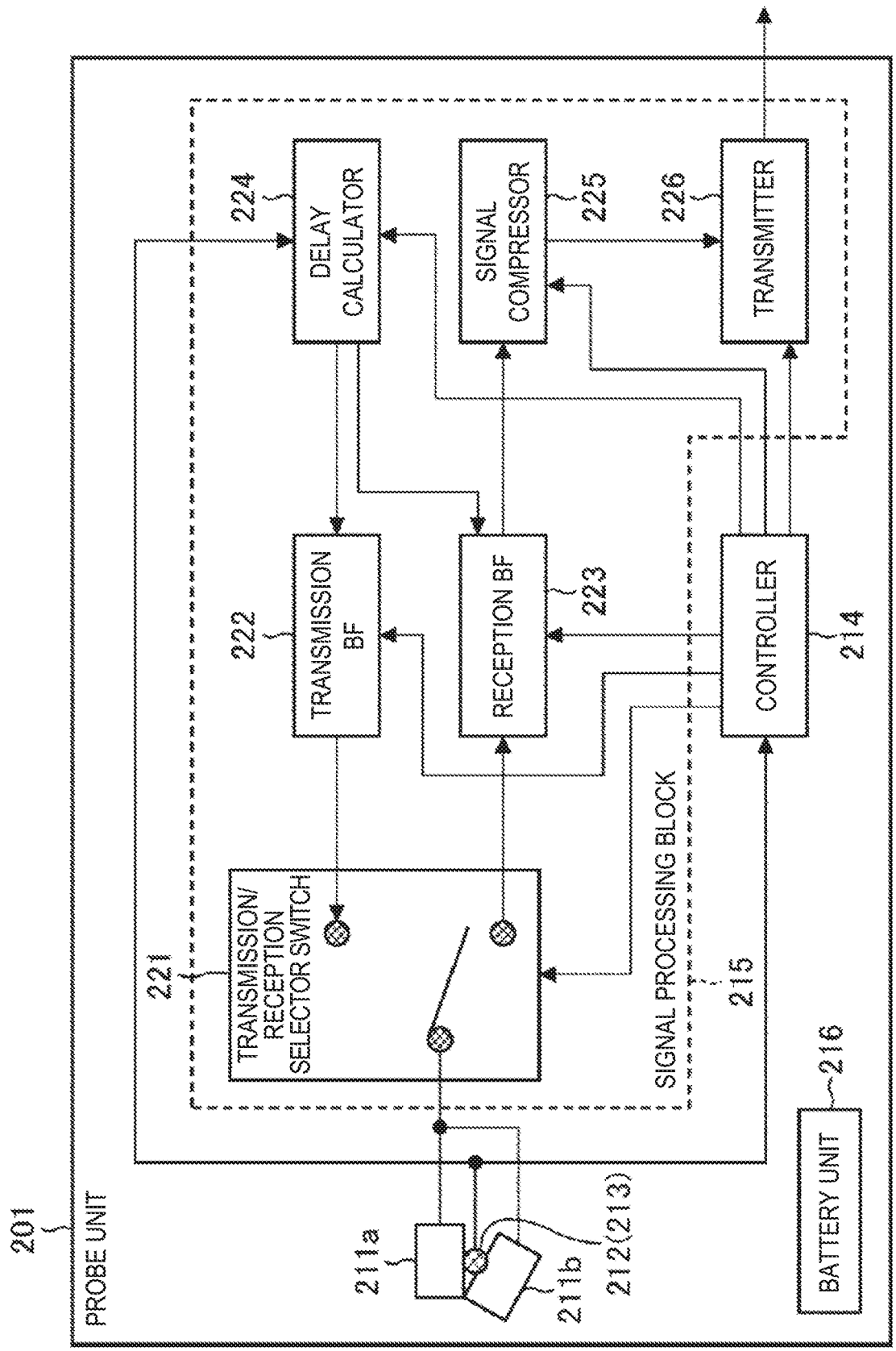
FIG. 10 is a block diagram showing another example of the probe unit.

FIG. 10 is a diagram showing another exemplary configuration of the probe unit of FIG. 1.

A probe unit 201 includes a probe 211a, a probe 211b, a rotating shaft 212, an angle sensor 213, a controller 214, a signal processing block 215, and a battery unit 216.

The signal processing block 215 is a block corresponds to the signal processing block 122 of FIG. 1. The signal processing block 215 includes a transmission/reception selector switch 221, a transmission BF (beamforming) 222, a reception BF (beamforming) 223, a delay calculator 224, a signal compressor 225, and a transmitter 226.

Figure 11:
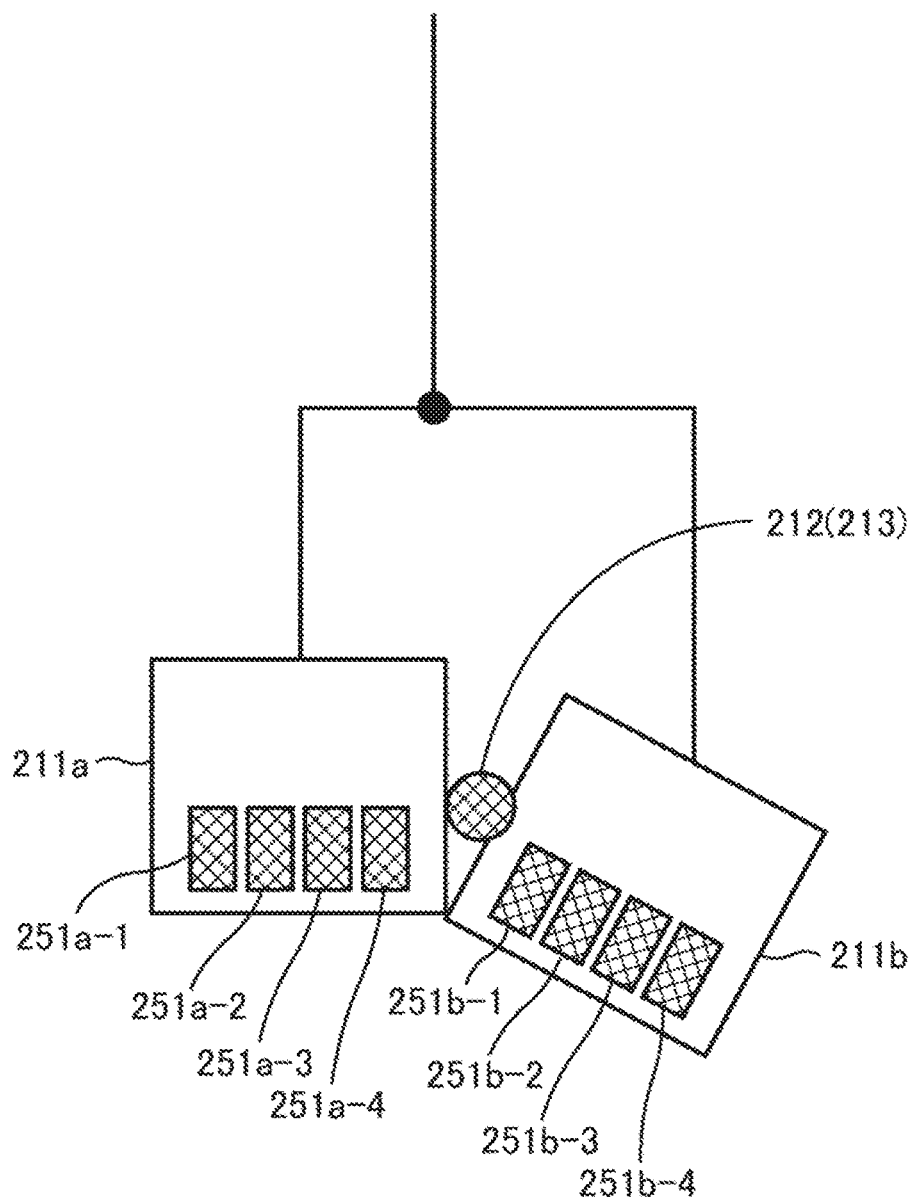
FIG. 11 is a schematic diagram showing an exemplary configuration of the probe.

The probe 211a, as shown in FIG. 11, includes vibrators 251a-1 to 251a-4. The vibrators 251a-1 to 251a-4 transmit an ultrasonic wave respectively under control of the transmission BF 222. Also, the vibrators 251a-1 to 251a-4 receive a reflected wave of the transmitted ultrasonic wave, and provide a received signal which shows intensity of the received reflected wave to the reception BF 223 via the transmission/reception selector switch 221.

The probe 211b, as shown in FIG. 11 and similar to probe 211a, includes vibrators 251b-1 to 251b-4. The vibrators 251b-1 to 251b-4 transmit an ultrasonic wave respectively under control of the transmission BF 222. Also, the vibrators 251b-1 to 251b-4 receive a reflected wave of the transmitted ultrasonic wave, and provide a received signal which shows intensity of the received reflected wave to the reception BF 223 via the transmission/reception selector switch 221.

The probes 211a and 211b as together correspond to the probe 120 of FIG. 1. The probes 211a and 211b are connected by a hinge structure which includes the rotating shaft 212, and a relative angle between the probes 211a and 211b can be changed around the rotating shaft 212 as a fulcrum shaft. As a result, a relative angle between the vibrators 251a-1 to 251a-4 of the probe 211a and the vibrators 251b-1 to 251b-4 of the probe 211b is changed.

Note that, hereinafter, if it is not necessary to distinguish the probes 211a and 211b individually, they are simply referred to as the probe 211. Also, if it is not necessary to distinguish the vibrators 251a-1 to 251a-4 individually, they are simply referred to as the vibrator 251a, and if it is not necessary to distinguish the vibrators 251b-1 to 251b-4 individually, they are simply referred to as the vibrator 251b.

Further, if it is not necessary to distinguish the vibrators 251a-1 to 251b-4 individually, they are simply referred to as the vibrator 251.

Further, the rotating shaft 212 has the angle sensor 213 built-in. The angle sensor 213 detects a rotating angle of the rotating shaft 212, and provides a sensor signal which shows the detected angle to the controller 214 and the delay calculator 224.

Here, the rotating shaft 212 rotates as the probe 211 moves. When the user moves the probe unit 201 small and slowly in order to clearly look at a position to be shot an ultrasonic image, a change of the rotating angle detected by the angle sensor 213 is small. On the other hand, when the user moves the probe unit 201 big and quickly in order to look for a position to be shot an ultrasonic image within a rough area on the body, the change of the rotating angle detected by the angle sensor 213 is large. That is, the rotating angle detected by the angle sensor 213 is one of the motion parameters which show a characteristic of the motion of the probe 211.

The controller 214 controls each part of the signal processing block 215 in response to the motion parameter detected by the angle sensor 213 (a magnitude of the change of the rotating shaft, for example).

The transmission/reception selector switch 221 of the signal processing block 215 selects one of the transmission BF 222 and the reception BF 223 by switching a built-in switch and connects to the probe 211.

Further, the transmission/reception selector switch 221 also carries out processes which correspond to the switch 161 of FIG. 2 and the switch 181 of FIG. 3. That is, when selecting the transmission BF 222, the transmission/reception selector switch 221 selects a vibrator 251 to be operated based on an analog signal from the transmission BF 222. When selecting the reception BF 223, the transmission/reception selector switch 221 determines which signal to be read from among the signals received by each vibrator of the vibrator 251 and selects the signal.

The transmission BF 222 corresponds to the DA converter 182 and the signal processor 183 of FIG. 3, and carries out transmission beamforming under control of the delay calculator 224, and converts processed RF data into an analog signal. That is, the transmission BF 222 controls a waveform of an ultrasonic beam formed by an ultrasonic wave transmitted from the each vibrator 251 by generating digital data and controlling a transmission timing or the like of the ultrasonic wave from the each vibrator 251 of the probe 211.

The reception BF 223 corresponds to the AD converter 162 and the signal processor 163 of FIG. 2, and carries out AD conversion for the signal from the transmission/reception selector switch 221 at a prescribed sampling rate under control of the delay calculator 224. That is, the reception BF 223 generates a signal which shows intensity of the reflected wave from each position of the object (hereinafter, referred to as reflected wave detected signal) by synthesizing the received signal provided from the each vibrator 251 of the each probe 211 by shifting a time. The reception BF 223 provides the generated reflected wave detected signal to the signal compressor 225.

The reception BF 223 carries out signal processing such as image enhancement and noise reduction for the data after beamforming (the reflected wave detected signal) as necessary.

The delay calculator 224 calculates a delay amount which shows a delay time in transmission by the each vibrator 251 of the probe 211 (hereinafter, referred to as transmission delay amount) based on a result of the rotating angle of the rotating shaft 212 detected by the angle sensor 213. Then, the delay calculator 224 controls transmission beamforming of the transmission BF 222 by providing the transmission delay amount to the transmission BF 222.

The delay calculator 224 calculates a delay amount which shows a delay time in reception by the each vibrator 251 of the probe 211 (hereinafter, referred to as reception delay amount) based on a result of the rotating angle of the rotating shaft 212 detected by the angle sensor 213. Then, the delay calculator 224 controls reception beamforming of the reception BF 223 by providing the reception delay amount to the reception BF 223.

The signal compressor 225 corresponds to the signal compressor 164 of FIG. 2, and compresses the digital data provided from the reception BF 223 in a prescribed compressed format. The signal compressor 225 provides the compressed data to the transmitter 226.

The transmitter 226 corresponds to the transmitter 165 of FIG. 2, and makes an addition to the data from the signal compressor 225 such as a redundant error correcting code for transmission error compensation, and transmits the data to the reception display apparatus 112 of FIG. 1 via a wireless IF not shown in the drawings. The transmitter 226 retransmits the data in order to compensate a transmission error.

The battery unit 216 is configured with a rechargeable battery and the like, and supplies the electric power to each part of the probe unit 201.

The controller 214 changes a processing parameter of the each part which constitutes the signal processing block 215 to lower a performance of the each part which constitutes the signal processing block 215 in order to reduce the electric power consumption accumulated in the battery unit 216.

The controller 214 controls ON and OFF of a function of the delay calculator 224 to lower the performance of the each part which constitutes the signal processing block 215.

In the probe unit 201, when the delay calculator 224 functions, the delay calculator 224 carries out control of the transmission BF 222 and the reception BF 223. Therefore, in this case, the controller 214 controls processing parameters of the transmission BF 222 and the reception BF 223 by controlling a parameter that the delay calculator 224 uses for calculation. Note that, even when the delay calculator 224 functions, the controller 214 is capable of controlling the processing parameters of the transmission BF 222 and the reception BF 223 as similar to the probe unit 111 of FIG. 1 described above.

The controller 214 controls the delay calculator 224 to change the processing parameter used in the transmission BF 222. That is, the controller 214 controls the delay calculator 224 to change the number of effective vibrators, the number of lines (a set number of transmission focal positions), a bit length of digital data, a sampling frequency, a combination of the vibrators 251 connected by the transmission/reception selector switch 221 and the like.

The controller 214 controls the delay calculator 224 to change the processing parameter used in the reception BF 223. That is, the controller 214 controls the delay calculator 224 to change the number of reception vibrators, the number of reception focal points, a sampling frequency of RF data, an ON/OFF in signal processing such as image enhancement and noise reduction, and a parameter which shows complexity of an algorithm.

On the other hand, when the delay calculator 224 does not function, the controller 214 controls the processing parameters of the transmission BF 222 and the reception BF 223 as similar to the probe unit 111 described above.

For example, the controller 214 controls the transmission selector switch 221 to change the number of reception vibrators. The controller 214 controls the transmission BF 222 to change the bit length of digital data, the sampling frequency, the number of lines, and the combination of the vibrators 251 connected by the transmission selector switch 221.

The controller 214 controls the reception BF 223 to change the number of reception focal points, a sampling frequency of RF data, an ON/OFF in signal processing such as image enhancement and noise reduction, and a parameter which shows complexity of an algorithm.

Further, the controller 214 controls the signal compressor 225 to control a data compression rate. The controller 214 controls the transmitter 226 to change a degree of adding an error correcting code or whether or not the error correction is added.

[Process in Probe Unit]

Figure 12:
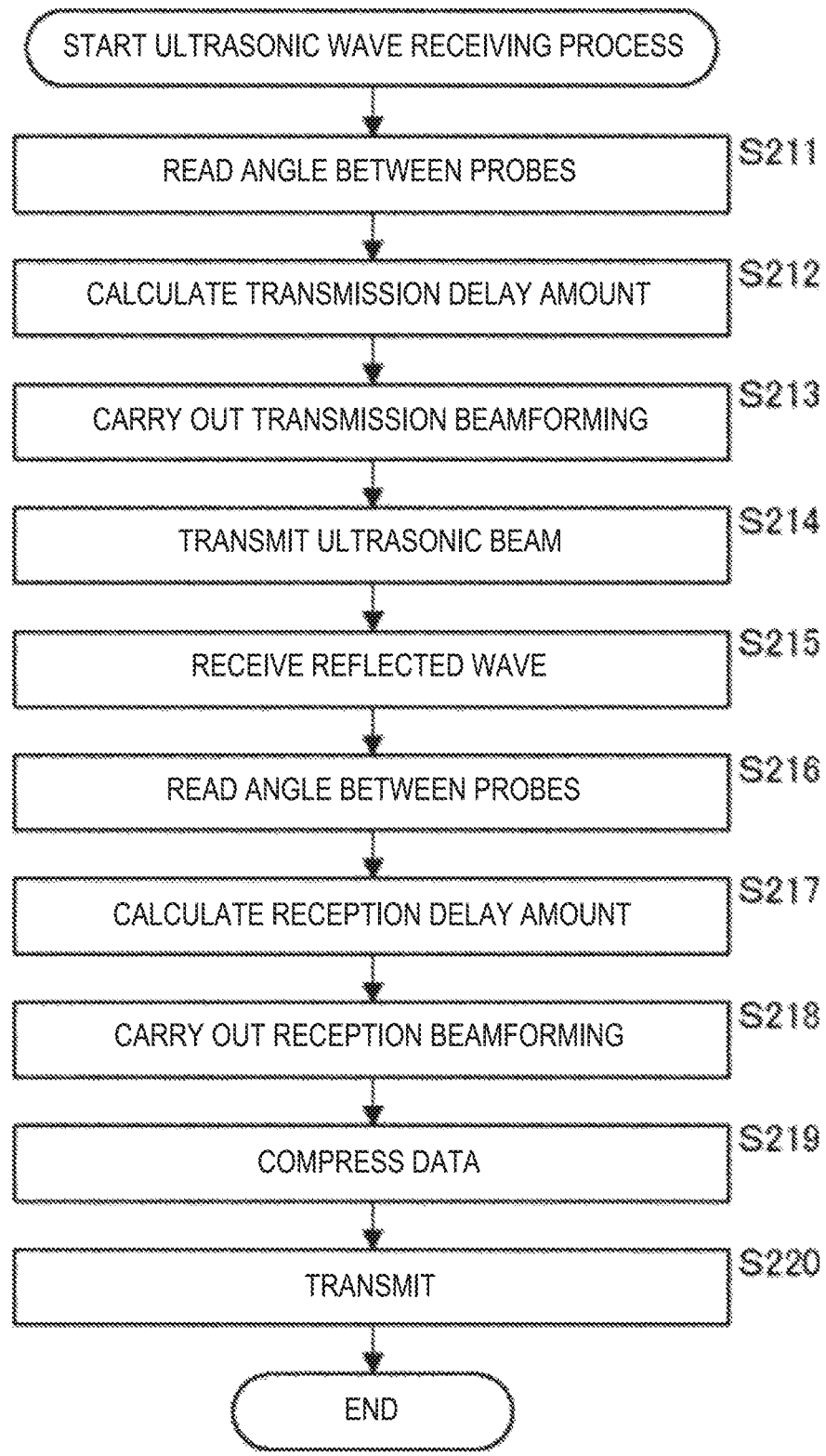
FIG. 12 is a flowchart illustrating an example of an ultrasonic wave transmission/reception process of the probe unit.

Next, an ultrasonic wave transmission/reception process carried out by the probe unit 201 will be descried with reference to the flowchart of FIG. 12. Note that this process begins, for example, upon receiving an input of a process start instruction via an input part not shown in the drawings.

At step S211, the delay calculator 224 reads an angle between the probes 211 based on a sensor signal provided by the angle sensor 213.

At step S212, the delay calculator 224 calculates a transmission delay amount.

Here, the probe unit 201 scans an ultrasonic beam (a transmission wave) transmitted from the each vibrator 251 of the probe 211 in a prescribed scanning direction (for example, in a radial pattern or in the direction perpendicular to a traveling direction of the ultrasonic beam).

Further, the probe unit 201 carries out an electronic focus of the ultrasonic beam. That is, the probe unit 201 switches the vibrator 251 to be used for transmission/reception of the ultrasonic beam (hereinafter, referred to as effective vibrator) while controls a transmission timing of the each effective vibrator and controls a phase of the ultrasonic wave transmitted from the each effective vibrator. Consequently, the focal position of the ultrasonic beam (hereinafter, referred to as transmission focal position) formed by the ultrasonic wave transmitted from the effective vibrator is controlled.

Note that, with respect to one scanning line, it may be possible to transmit an ultrasonic beam only once by setting one transmission focal position, or it may also be possible to carry out a multi-stage focus in which an ultrasonic beam is transmitted several times by setting a plurality of transmission focal positions having different depths. However, on the one hand, the more transmission focal positions are set, the more detailed ultrasonic image can be obtained. On the other hand, the frame rate becomes lower because the number of ultrasonic beam transmission/reception increases. The set number of transmission focal positions is one of processing parameters, and is, for example, controlled by the controller 214 in response to the motion parameter from the angle sensor 213.

Also, a shape of a scanning surface which is an area where the ultrasonic beam is scanned may be, for example, set by the user, or may be set automatically based on an angle between the probes 211. It may also be controlled by the controller 214.

The delay calculator 224 sets a plurality of transmission focal positions used for a shot of one frame of an ultrasonic image based on the processing parameters such as the number of scanning lines, the number of transmission focal positions per scanning line. Then, the delay calculator 224 selects a transmission focal point of an ultrasonic beam to be transmitted next from among the transmission focal positions.

Further, the delay calculator 224 selects a plurality of effective vibrators to be used for the next transmission/reception of an ultrasonic beam in response to the selected transmission focal position. At this time, the effective vibrators may range over the two probes 120.

Note that the number of effective vibrators is one of the processing parameters, and is controlled by the controller 214 in response to the motion parameter from the angle sensor 213, but is fixable. In the latter case, for example, the number of effective vibrators is fixed to a prescribed value (such as 4), and positions of the effective vibrators are shifted in response to the transmission focal positions.

On the other hand, in the former case, for example, not only the positions of the effective vibrators, but also the number of effective vibrators are changed in response to the transmission focal positions and the motion parameter from the angle sensor 213. For example, after a set of the vibrators 251a-1 to 251a-3 is set to the effective vibrator at first, the number and the positions of effective vibrators can be changed in the following order. That is, in the order of a set of the vibrators 251a-2 to 251a-4, a set of the vibrators 251a-4 and 251b-1, a set of the vibrators 251b-1 to 251b-3, and a set of the vibrators 251b-2 to 251b-4.

Or, it may also be possible to set all vibrators 251 of the probe 211a and of the probe 211b to be the effective vibrators on a constant basis.

Note that it is not necessary to match the vibrator 251 used for transmission with the vibrator 251 used for reception. For example, it may also be possible to receive a reflected wave of an ultrasonic beam by a set of the vibrator 251 used for reception which is a different combination of a set of the vibrator 251 used for transmission.

Note that, hereinafter, as one example, the same vibrators 251 will be used for transmission/reception of an ultrasonic wave unless otherwise especially noted.

Also, the delay calculator 224 calculates a relative position between the effective vibrators based on an angle between the probes 211, and known geometry information. Here, the geometry information includes, for example, a distance between the each vibrator 251 of the each probe 211, and a distance from the rotating shaft 212 to the each vibrator 251.

Further, the delay calculator 224 calculates a distance between each effective vibrator and the transmission focal position or a difference of the distances.

Further, the delay calculator 224 calculates a transmission delay amount which shows a time by which a timing of transmitting an ultrasonic wave from each effective vibrator is delayed based on a difference of time that an ultrasonic wave transmitted from the effective vibrator reaches the transmission focal position. That is, the delay calculator 224 calculates the transmission delay amount with respect to each effective vibrator to match a focal point which is formed by an ultrasonic wave transmitted from each effective vibrator with a set transmission focal position.

Note that other parameter such as a display mode or a gain setting might be used for the calculation of the transmission delay amount other than the parameters described above.

The delay calculator 224 transmits information showing the transmission delay amount with respect to each effective vibrator to the transmission BF 222.

At step S213, the transmission BF 222 carries out transmission beamforming. To be more specific, the transmission BF 222 calculates a waveform of an ultrasonic wave transmitted from each effective vibrator based on the transmission delay amount of each effective vibrator calculated by the delay calculator 224.

At step S214, the probe unit 201 transmits an ultrasonic beam. To be more specific, the transmission/reception selector switch 221 switches a position of the switch to the transmission BF 222 side. The transmission BF 222 provides a control signal to each effective vibrator via the transmission/reception selector switch 221 to transmit an ultrasonic wave having the waveform calculated at step S213.

Then, an ultrasonic beam which is formed by the ultrasonic wave transmitted from each effective vibrator forms a focal point at the transmission focal position set at step S212.

At step S215, the probe unit 111 receives a reflected wave. To be more specific, the transmission/reception selector switch 221 switches a position of the switch to the reception BF 223 side. Then, each effective vibrator receives a reflected wave of the ultrasonic beam transmitted at step S214. Each effective vibrator converts intensity of the received reflected wave into an electrical signal, and provides, to the reception BF 223 via the transmission/reception selector switch 221, a received signal which shows a time-series change of the intensity of the received reflected wave.

The reception BF 223 amplifies the received signal from each effective vibrator and carries out AD conversion for the amplified signal into a digital signal. Note that the AD (digital data) bit length and the AD sampling rate of this time are controlled by the controller 214 in response to a magnitude of the motion parameter from the angle sensor 213.

At step S216, the delay calculator 224 reads an angle between the probes 120 as similar to the process at step S211.

At step S217, the delay calculator 224 calculates a reception delay amount.

Here, the probe unit 111 carries out a dynamic focal in which a reflected wave (a received wave) transmitted from the effective vibrator is received while changing a focal point (hereinafter, referred to as reception focal point) by digital processing per one ultrasonic beam transmission.

The delay calculator 224 sets a plurality of reception focal points on the scanning line of the ultrasonic beam transmitted at step S214.

Note that a set number of reception focal points is set based on the requested image quality or the frame rate, for example. However, it may also be controlled by the controller 214 in response to the motion parameter from the angle sensor 213. Normally, more of the reception focal positions are set than the transmission focal positions.

Further, the delay calculator 224 calculates a relative position between the effective vibrators based on the angle of the probes 211, and known geometry information. Then, the delay calculator 224 calculates distances between all the set reception focal points and each effective vibrator, or differences of the distances between all the set reception focal points and the each effective vibrator based on the relative positions between the effective vibrators.

Here, a reflected wave from a reception focal point reaches the each effective vibrator by a time difference according to the distance from the reception focal point. Therefore, a reflected wave detected signal can be generated, which shows intensity of the reflected wave from the reception focal point, by synthesizing the received signals provided from the each effective vibrator with the time difference.

Then, the delay calculator 224 calculates the reception delay amount which shows a time shifted amount of the each received signal in synthesizing the received signals generated at the each vibrator based on the time difference that the reflected wave from the each reception focal position reaches the each effective vibrator.

At step S218, the reception BF 223 carries out reception beamforming. To be more specific, the reception BF 223 selects one reception focal point, synthesizes the received signal from the each effective vibrator by shifting a time based on the reception delay amount of the selected reception focal point. Consequently, the reflected wave detected signal which shows the intensity of the reflected wave from the selected reception focal point is generated.

The reception BF 223 carries out a similar process for all the reception focal points. In doing so, the reflected wave detected signal of the each reception focal point set on the current scanning line is generated.

The reception BF 223 transmits the digital data as the reflected wave detected signal of the each reception focal point to the signal compressor 225.

At step S219, the signal compressor 225 compresses the digital data from the reception BF 223 in a prescribed compressed format. The bit rate of this time is controlled by the controller 214 in response to the motion parameter of the angle sensor 213. The signal compressor 225 provides the compressed data to the transmitter 226.

At step S220, the transmitter 226 makes an addition to the data from the signal compressor 225 such as a redundant error correcting code for transmission error compensation, and transmits the data to the reception display apparatus 112 of FIG. 1 via a wireless IF not shown in the drawings. The addition of the error correction or the like of this time are controlled by the controller 214 in response to an output from the angle sensor 213.

As described above, a received ultrasonic wave is subject to the series of processes, and the processed data is transmitted to the reception display apparatus 112 via wireless communication. In response to the above processes, the reception display apparatus 112 receives the data from the probe unit 201 to display an ultrasonic image described by reference to FIG. 7.

[Flow of Control Process]

Figure 13:
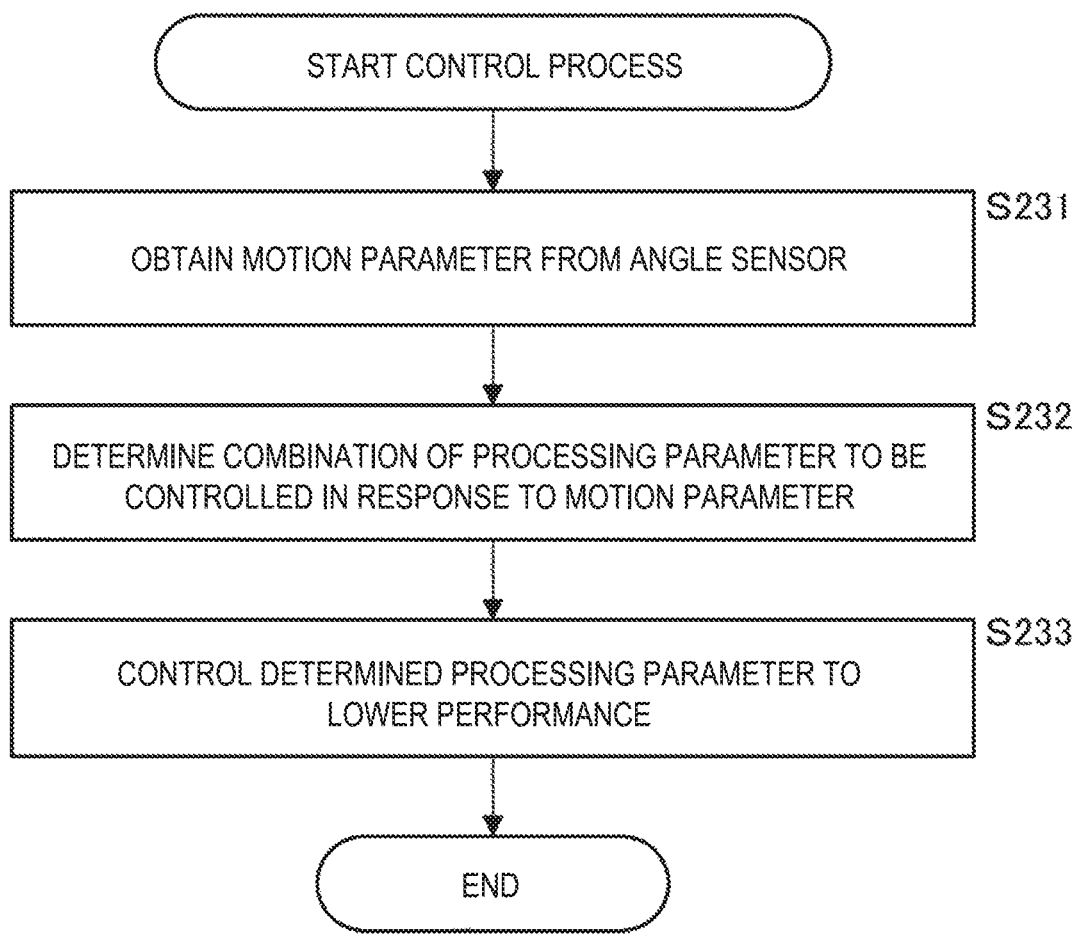
FIG. 13 is a flowchart illustrating an example of a control process in the probe unit.

Next, a control process in the probe unit 201 will be described with reference to the flowchart of FIG. 13.

The angle sensor 213 detects a motion of the probe 211, and provides a motion parameter as information of the detected motion to the controller 214. At step S231, the controller 214 obtains the motion parameter from the angle sensor 213. At step S232, the controller 214 determines, described by reference to FIG. 5, a parameter to be controlled to lower a performance in response to the obtained motion parameter.

At step S233, the controller 214 controls the parameter determined at step S232 to lower the performance. In doing so, among the each part of the signal processing block 215, the part which carries out a process by using the parameter is controlled. At this time, processing parameters which have not been determined by the process at step S232 is controlled to perform standard operation.

As described above, the image quality of an ultrasonic image desired by the user can be known from the motion of the probe unit 201 (the probe 211) by the user. Therefore, the signal processing system 101 controls the process of the each part of the signal processing block 215 in response to the motion of the probe 211. Especially, the probe unit 201 controls the processing parameter to lower the performance in the signal processing when the motion parameter which shows a characteristic of the motion of the probe 211 is large.

Therefore, when the user moves the probe unit 201 small or slowly in order to clearly look at a position to be shot an ultrasonic image, the image quality can be preferentially enhanced over reduction of the electric power consumption.

On the other hand, when the user moves the probe unit 201 big and quickly in order to look for a position within a rough area on the body, the electric power consumption can be preferentially reduced over enhancement of the image quality.

Accordingly, the life of the battery unit 216 of the probe unit 201 can be maintained.

As described above, the signal processing system 101 controls the processing parameter to lower the signal processing performance when the motion parameter which shows a characteristic of the motion of the probe is large. Therefore, even during diagnosis, the electric power consumption is reduced in a positive manner, and as a result, the life of the battery in the probe unit can be maintained.

Also, an increase of temperature of the probe or the like can be reduced. Further, the life of the probe can be maintained.

Note that, in the above description, an example is explained in which the acceleration sensor and the angle sensor are used as a detector for detecting the motion of the probe. However, the detector is not limited to those sensors. Any sensor is applicable if the sensor is capable of detecting the motion of the probe. For example, the sensor might be a gyro sensor.

Furthermore, in FIG. 1, an example is described in which the reception display apparatus 112 receives data and generates an image. However, it may also be possible that the prove unit 111 generates and compresses an image and then transmits the image to the reception display apparatus 112.

The series of processes described above can be executed by hardware but can also be executed by software. When the series of processes is executed by software, a program that constructs such software is installed into a computer. Here, the expression "computer" includes a computer in which dedicated hardware is incorporated and a general-purpose personal computer or the like that is capable of executing various functions when various programs are installed.

[Exemplary Configuration of Computer]

Figure 14:
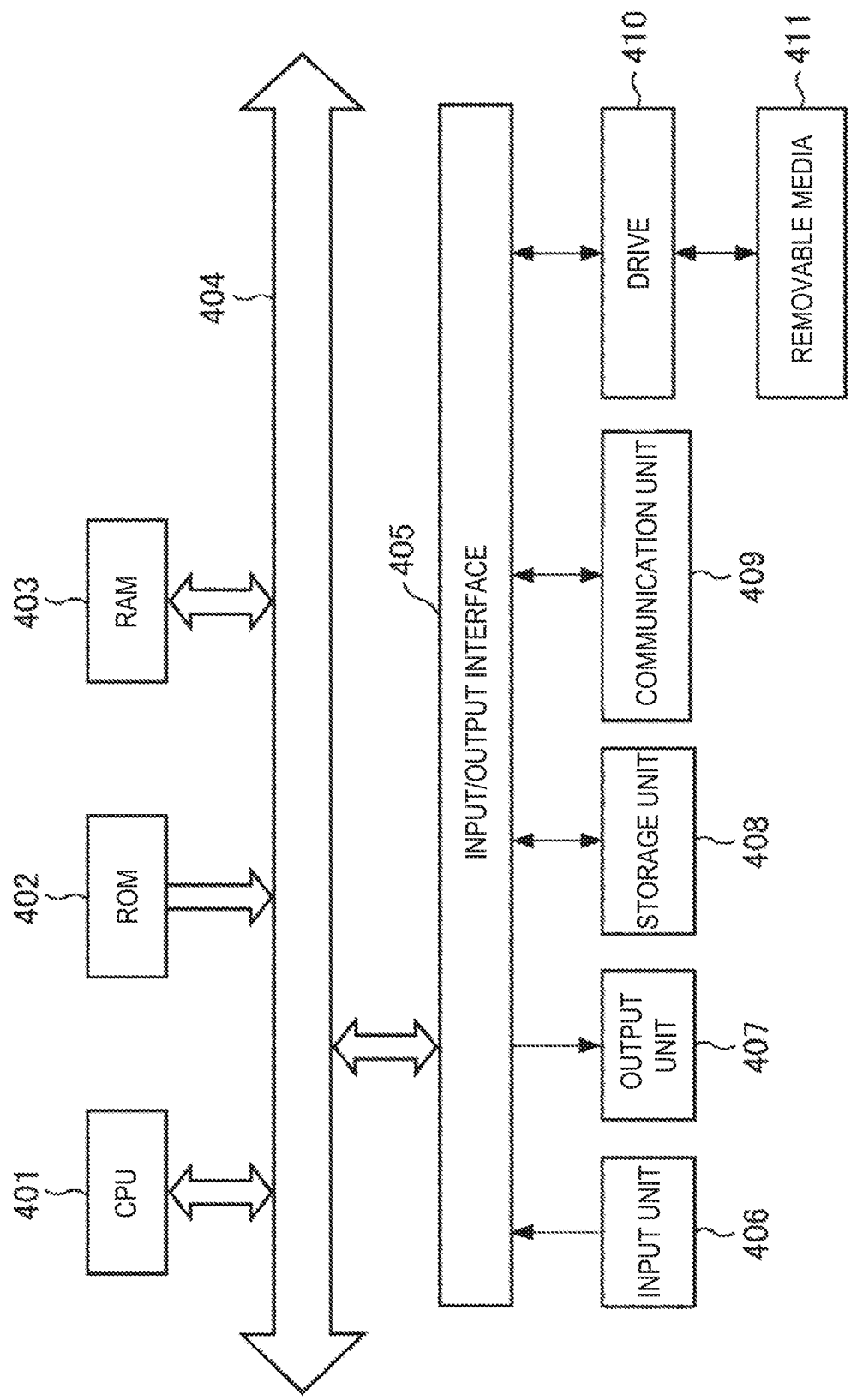
FIG. 14 is a block diagram showing an exemplary configuration of a computer.

FIG. 14 is a block diagram showing an exemplary configuration of the hardware of a computer that executes the series of processes described earlier according to a program.

In the computer, a central processing unit (CPU) 401, a read only memory (ROM) 402 and a random access memory (RAM) 403 are mutually connected by a bus 404.

An input/output interface 405 is also connected to the bus 404. An input unit 406, an output unit 407, a storage unit 408, a communication unit 409, and a drive 410, are connected to the input/output interface 405.

The input unit 406 is configured from a keyboard, a mouse, a microphone or the like. The output unit 407 configured from a display, a speaker or the like. The storage unit 408 is configured from a hard disk, a non-volatile memory or the like. The communication unit 409 is configured from a network interface or the like. The drive 410 drives a removable media 411 such as a magnetic disk, an optical disk, a magneto-optical disk, a semiconductor memory or the like.

In the computer configured as described above, the CPU 401 loads a program that is stored, for example, in the storage unit 408 onto the RAM 403 via the input/output interface 405 and the bus 404, and executes the program. Thus, the above-described series of processing is performed.

Programs to be executed by the computer (the CPU 401) are provided being recorded in the removable media 411 which is a packaged media or the like. Also, programs may be provided via a wired or wireless transmission medium, such as a local area network, the Internet or digital broadcasting.

In the computer, by inserting the removable media 411 into the drive 410, the program can be installed in the storage unit 408 via the input/output interface 405. Further, the program can be received by the communication unit 409 via a wired or wireless transmission media and installed in the storage unit 408. Moreover, the program can be installed in advance in the ROM 402 or the storage unit 408.

Note that the program executed by the computer may be a program in which processes are carried out in a time series in the order described in this specification or may be a program in which processes are carried out in parallel or at necessary timing, such as when the processes are called.

Further, in this specification, the terms of the system represent an overall apparatus which is composed of a plurality of devices, blocks, means or the like.

Note that the embodiments of the present disclosure are not limited to the above examples, of course, and various alternations and modifications within the scope of the present disclosure may occur.

It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) A signal processing apparatus including:
a signal processor for processing a signal to be received from or to be transmitted to a vibrator constituting a probe; and
a controller for controlling a signal processing parameter of the signal processor to lower a performance of the signal processor when a motion parameter showing a characteristic of a motion of the probe is large.

(2) The signal processing apparatus according to (1),
wherein the signal processing parameter is an external signal processing parameter used in signal processing in relation to transmission, and is an ultrasonic signal processing parameter used in signal processing in relation to ultrasonic treatment, and
wherein the controller controls the ultrasonic signal processing parameter and the external signal processing parameter by setting a priority to lower the performance.

(3) The signal processing apparatus according to (2),
wherein the signal processing parameter is the external signal processing parameter used in signal processing in relation to transmission, the ultrasonic signal processing parameter used in signal processing in relation to ultrasonic treatment, and an internal signal processing parameter used in signal transmission in relation to AD or DA conversion, and
wherein the controller controls the ultrasonic signal processing parameter, the external signal processing parameter, and the internal signal processing parameter by setting a priority to lower the performance.

(4) The signal processing apparatus according to (3),
wherein the signal processing parameter is the external signal processing parameter used in signal processing in relation to transmission, the ultrasonic signal processing parameter used in signal processing in relation to ultrasonic treatment, and the internal signal processing parameter used in signal transmission in relation to AD or DA conversion, and
wherein the controller controls the internal signal processing parameter, the ultrasonic signal processing parameter, and the external signal processing parameter in the stated order in response to a magnitude of the motion parameter to lower the performance.

(5) The signal processing apparatus according to (3) or (4),
wherein the internal signal processing parameter is an AD sampling rate, and an AD bit length, and
wherein the controller controls the AD sampling rate, and the AD bit length in the stated order in response to the magnitude of the motion parameter to lower the performance.

(6) The signal processing apparatus according to any one of (3) to (5),
wherein the ultrasonic signal processing parameter is the number of transmission/reception vibrators, and the number of transmission beams, and
wherein the controller controls the number of transmission/reception vibrators, and the number of transmission beams in the stated order in response to the magnitude of the motion parameter to lower the performance.

(7) The signal processing apparatus according to any one of (3) to (6),
wherein the external signal processing parameter is an error correction, a bit rate, a resolution, and a frame rate, and
wherein the controller controls the error correction, the bit rate, the resolution, and the frame rate in the stated order in response to the magnitude of the motion parameter to lower the performance.

(8) The signal processing apparatus according to any one of (1) to (7), further including:
a focal position controller for controlling a transmission focal position as a focal position of a transmission wave transmitted by a plurality of the vibrators, and a reception focal position as a focal position of a reception wave received by a plurality of the vibrators based on positional information relating to a relative position of a plurality of the vibrators obtained from the motion of the probe, and
wherein the controller controls a parameter used for control by the focal point controller to lower the performance of the signal processor when the motion parameter is large.

(9) The signal processing apparatus according to any one of (1) to (8), further including:
a sensor for detecting the motion of the probe.

(10) A control method performed by a signal processing apparatus, which includes a signal processor for processing a signal to be received from or to be transmitted to a vibrator constituting a probe, the control method including:
controlling a signal processing parameter of the signal processor to lower a performance of the signal processor when a motion parameter showing a characteristic of a motion of the probe is large.

(11) A signal processing system including:
a first signal processing apparatus including
a signal processor for processing a signal to be received from or to be transmitted to a vibrator constituting a probe,
a controller for controlling a signal processing parameter of the signal processor to lower a performance of the signal processor when a motion parameter showing a characteristic of a motion of the probe is large, and a transmitter for transmitting the signal processed by the signal processor; and a second signal processing apparatus including a receiver for receiving the signal from the first signal processing apparatus, and a generator for generating an ultrasonic image based on the signal received by the receiver.

(12) A signal processing method performed by a first signal processing apparatus, which includes a signal processor for processing a signal to be received from or to be transmitted to a vibrator constituting a probe, the signal processing method including:

controlling a signal processing parameter of the signal processor to lower a performance of the signal processor when a motion parameter showing a characteristic of a motion of the probe is large;

processing the signal to be received from or to be transmitted to the vibrator; and transmitting the processed signal, and the signal processing method performed by a second signal processing apparatus, including:

receiving the signal from the first signal processing apparatus; and generating an ultrasonic image based on the received signal.

What is claimed is:

1. A wireless medical device, comprising:
a wireless interface configured to output a signal to an external device, wherein
the signal represents an image of a body of a patient, and
the external device generates medical image data corresponding to the image of the body of the patient based on the signal; and
circuitry configured to:
set a priority for each of a plurality of processes of the wireless medical device, wherein the plurality of processes includes at least one first process for wireless transmitting and at least one second process for an internal signal processing; and
control, based on a value of a characteristic of a motion of the wireless medical device and the priority set for each of the plurality of processes reduction of electric power consumption of the at least one first process for the wireless transmitting and the at least one second process for the internal signal processing in the wireless medical device, wherein
the value is larger than a threshold value, and
the reduction of electric power consumption of the at least one second process for the internal signal processing comprises reduction of an analog/digital sampling rate and an analog/digital bit length.

2. The wireless medical device according to claim 1, wherein
the reduction of electric power consumption of the at least one first process for the wireless transmitting and the at least one second process for the internal signal processing further comprises reduction of a speed of the at least one first process for the wireless transmitting and the at least one second process for the internal signal processing, and
the reduction of the speed is based on the value that is larger than the threshold value.

3. The wireless medical device according to claim 1, wherein
the reduction of electric power consumption of the at least one first process for the wireless transmitting and the at least one second process for the internal signal processing comprises reduction of at least one of an operation clock, a transmission speed, a number of cores to perform the at least one first process for the wireless transmitting and the at least one second process for the internal signal processing, respectively, or a number of threads for the at least one first process for the wireless transmitting and the at least one second process for the internal signal processing, respectively, and
the reduction is based on the value that is larger than the threshold value.

4. The wireless medical device according to claim 1, wherein
the reduction of electric power consumption of the at least one first process for the wireless transmitting comprises reduction of at least one of a bit rate, resolution, or a frame rate, and
the reduction is based on the value that is larger than the threshold value.

5. The wireless medical device according to claim 1, further comprising a battery configured to supply electric power to at least one component of the wireless medical device.

6. The wireless medical device according to claim 1, further comprising a plurality of vibrators configured to output an ultrasonic beam to the body of the patient.

7. The wireless medical device according to claim 6, wherein
the plurality of vibrators is further configured to:
transmit a transmission wave to the body of the patient; and
receive a reception wave from the body of the patient, and
the circuitry is further configured to:
control a transmission focal position as a focal position of the transmission wave transmitted by the plurality of vibrators; and
control a reception focal position as a focal position of the reception wave received by the plurality of vibrators.

8. The wireless medical device according to claim 1, wherein the characteristic of the motion of the wireless medical device includes an acceleration of the wireless medical device.

9. The wireless medical device according to claim 1, further comprising a sensor configured to detect the motion of the wireless medical device.

10. The wireless medical device according to claim 1, wherein
the circuitry is further configured to control, based on pressure information, the reduction of electric power consumption of the at least one first process for the wireless transmitting and the at least one second process for the internal signal processing in the wireless medical device, and
the pressure information corresponds to a pressure applied to the body of the patient by the wireless medical device.

11. The wireless medical device according to claim 10, further comprising a pressure sensor configured to detect the pressure applied to the body of the patient by the wireless medical device.

12. A control method, comprising:
in a wireless medical device:
setting a priority for each of a plurality of processes of the wireless medical device, wherein the plurality of processes includes at least one first process for wireless transmitting and at least one second process for an internal signal processing; and controlling, based on a value of a characteristic of a motion of the wireless medical device and the priority set for each of the plurality of processes reduction of electric power consumption of the at least one first process for the wireless transmitting and the at least one second process for the internal signal processing in the wireless medical device, wherein the value is larger than a threshold value, and the reduction of electric power consumption of the at least one second process for the internal signal processing comprises reduction of an analog/digital sampling rate and an analog/digital bit length.

13. A wireless medical system, comprising:

a wireless medical device including:

a wireless interface configured to output a signal representing an image of a body of a patient; and circuitry configured to:

set a priority for each of a plurality of processes of the wireless medical device, wherein the plurality of processes includes at least one first process for wireless transmitting and at least one second process for an internal signal processing; and control, based on a value of a characteristic of a motion of the wireless medical device and the priority set for each of the plurality of processes reduction of electric power consumption of the at least one first process for the wireless transmitting and the at least second process for the internal signal processing in the wireless medical device, wherein the value is larger than a threshold value, and the reduction of electric power consumption of the at least second process for the internal signal processing comprises reduction of an analog/digital sampling rate and an analog/digital bit length; and reception circuitry configured to:

receive the signal; and generate medical image data corresponding to the image of the body of the patient based on the received signal.

14. The wireless medical system according to claim 13, wherein the wireless medical device further includes a battery configured to supply electric power to at least one component of the wireless medical device.

* * * * *